United States Patent
Greengard et al.

(10) Patent No.: US 9,605,041 B2
(45) Date of Patent: Mar. 28, 2017

(54) REGULATORY PROTEINS AND INHIBITORS

(75) Inventors: Paul Greengard, New York, NY (US); Wenjie Luo, New York, NY (US); Gen He, New York, NY (US); Peng Li, New York, NY (US); Lawrence Wennogle, New York, NY (US)

(73) Assignees: INTRA-CELLULAR THERAPIES, INC., New York, NY (US); THE ROCKEFELLER UNIVERSITY, New York, NY (US)

( * ) Notice: Subject to any disclaimer, the term of this patent is extended or adjusted under 35 U.S.C. 154(b) by 974 days.

(21) Appl. No.: 13/367,049

(22) Filed: Feb. 6, 2012

(65) Prior Publication Data

US 2013/0149309 A1 Jun. 13, 2013

Related U.S. Application Data

(63) Continuation of application No. PCT/US2010/002173, filed on Aug. 5, 2010.

(60) Provisional application No. 61/231,462, filed on Aug. 5, 2009.

(51) Int. Cl.
| | |
|---|---|
| C07K 16/40 | (2006.01) |
| C12N 15/113 | (2010.01) |
| C07K 14/47 | (2006.01) |
| A01K 67/027 | (2006.01) |
| A61K 39/00 | (2006.01) |
| G01N 33/68 | (2006.01) |
| A61K 31/506 | (2006.01) |
| C07K 16/18 | (2006.01) |
| C12Q 1/68 | (2006.01) |
| A61K 38/00 | (2006.01) |

(52) U.S. Cl.
CPC ...... *C07K 14/4705* (2013.01); *A01K 67/0275* (2013.01); *A61K 31/506* (2013.01); *A61K 39/0007* (2013.01); *C07K 16/18* (2013.01); *C12N 15/113* (2013.01); *C12Q 1/686* (2013.01); *C12Q 1/6827* (2013.01); *G01N 33/6896* (2013.01); *A01K 2207/05* (2013.01); *A01K 2217/058* (2013.01); *A01K 2217/15* (2013.01); *A01K 2217/203* (2013.01); *A01K 2227/105* (2013.01); *A01K 2267/0312* (2013.01); *A61K 38/00* (2013.01); *G01N 2800/2821* (2013.01)

(58) Field of Classification Search
None
See application file for complete search history.

(56) References Cited

U.S. PATENT DOCUMENTS

| | | |
|---|---|---|
| 5,272,055 A | 12/1993 | Haley |
| 5,294,612 A | 3/1994 | Bacon et al. |
| 5,385,915 A | 1/1995 | Buxbaum et al. |
| 5,393,755 A | 2/1995 | Neustadt et al. |
| 5,521,184 A | 5/1996 | Zimmermann |
| 5,543,520 A | 8/1996 | Zimmermann |
| 5,719,283 A | 2/1998 | Bell et al. |
| 5,733,914 A | 3/1998 | Blankley et al. |
| 5,744,346 A | 4/1998 | Chrysler et al. |
| 5,777,195 A | 7/1998 | Fienberg et al. |
| 5,824,683 A | 10/1998 | McKittrick et al. |
| 5,849,770 A | 12/1998 | Head et al. |
| 5,885,834 A | 3/1999 | Epstein |
| 5,939,419 A | 8/1999 | Tulshian et al. |
| 5,962,492 A | 10/1999 | Warrellow |
| 6,013,621 A | 1/2000 | Nishi et al. |
| 6,107,301 A | 8/2000 | Aldrich et al. |
| 6,133,273 A | 10/2000 | Gilbert et al. |
| 6,147,073 A | 11/2000 | Battistini et al. |
| 6,235,742 B1 | 5/2001 | Bell et al. |
| 6,235,746 B1 | 5/2001 | Davis et al. |
| 6,316,444 B1 | 11/2001 | Hunt et al. |
| 6,333,167 B1 | 12/2001 | Quinet et al. |
| 6,423,716 B1 | 7/2002 | Matsuno et al. |
| 6,440,698 B1 | 8/2002 | Gurney et al. |
| 6,451,838 B1 | 9/2002 | Moon et al. |
| 6,492,371 B2 | 12/2002 | Roylance |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,649,908 B2 | 11/2003 | Apffel et al. |

(Continued)

FOREIGN PATENT DOCUMENTS

| | | |
|---|---|---|
| AU | 2005201482 A1 | 5/2005 |
| DE | 19931206 A1 | 1/2001 |

(Continued)

OTHER PUBLICATIONS

He et al (Nature 467: 95- 98, 2010).*
Chu et al (J Alz Dis 41: 729-737, 2014—abstract only).*
Chu et al (Biol Psychiat 77: 720-728, 2015).*
Borchelt, et al., "Familial Alzheimer's Disease-Linked Presenilin 1 Variants Elevate Aβ1-42/1-40 Ratio In Vitro and In Vivo," Neuron. (1996) 17: 1005-1013.
Cancino, G., et al., "STI571 prevents apoptosis, *tau* phosphorylation and behavioral impairments induced by Alzheimer's β-amyloid deposits", *Brain*, 2008, vol. 131, p. 2425-2442.
De Strooper, et al., "A Presenilin-I-Depenedent β-Secretase-Like Protease Mediates Release of Notch Intracelllular Domain," Nature (1999) 398: 518-522.

(Continued)

Primary Examiner — Daniel E Kolker
Assistant Examiner — Aditi Dutt
(74) Attorney, Agent, or Firm — Hoxie & Associates LLC

(57) ABSTRACT

The invention provides a previously uncharacterized protein (gamma secretase activating protein or gSAP) that activates γ-secretase to produce β-amyloid protein (Aβ). Deposition of Aβ has been associated with Alzheimer's disease and other pathologies. The invention thus additionally provides, e.g., screening methods and novel research tools, inhibitors of this novel protein, and methods of diagnosis, treatment and control of Alzheimer's disease and other neurodegenerative conditions associated with deposition of Aβ.

3 Claims, 9 Drawing Sheets

(56) References Cited

U.S. PATENT DOCUMENTS

| | | |
|---|---|---|
| 6,670,368 B1 | 12/2003 | Breault et al. |
| 6,693,099 B2 | 2/2004 | Degenhardt |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,320,785 B2 | 1/2008 | Greengard et al. |
| 7,910,586 B2 | 3/2011 | Netzar et al. |
| 8,598,171 B2 | 12/2013 | Netzar et al. |
| 9,157,906 B2 | 10/2015 | Greengard et al. |
| 2002/0025540 A1 | 2/2002 | Roberts et al. |
| 2002/0077274 A1 | 6/2002 | Roylance |
| 2002/0128319 A1 | 9/2002 | Koo et al. |
| 2002/0147197 A1 | 10/2002 | Newman et al. |
| 2003/0069246 A1 | 4/2003 | Darrow et al. |
| 2003/0162782 A1 | 8/2003 | Grossman et al. |
| 2003/0195205 A1 | 10/2003 | DeNinno |
| 2003/0198594 A1 | 10/2003 | Collins et al. |
| 2003/0211040 A1 | 11/2003 | Greengard et al. |
| 2004/0023989 A1 | 2/2004 | Fryburg |
| 2004/0087517 A1 | 5/2004 | Burnet et al. |
| 2004/0171823 A1 | 9/2004 | Nadler et al. |
| 2005/0048573 A1 | 3/2005 | Artis et al. |
| 2005/0075795 A1 | 4/2005 | Pandit |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2009/0137549 A1 | 5/2009 | Edward et al. |
| 2010/0087450 A1 | 4/2010 | Mates et al. |
| 2010/0173878 A1 | 7/2010 | Li et al. |
| 2010/0173924 A1 | 7/2010 | Li et al. |
| 2010/0184778 A1 | 7/2010 | Li et al. |
| 2010/0323997 A1 | 12/2010 | Fienberg et al. |
| 2012/0053190 A1 | 3/2012 | Fienberg |

FOREIGN PATENT DOCUMENTS

| | | |
|---|---|---|
| EP | 0063381 A1 | 10/1982 |
| EP | 0201188 A2 | 12/1986 |
| EP | 0949242 | 10/1999 |
| EP | 1136485 | 9/2001 |
| EP | 0911333 A1 | 4/2002 |
| EP | 1 533 304 | 5/2005 |
| GB | 2151629 A | 7/1985 |
| JP | 53031694 A | 3/1978 |
| JP | A-11-043499 | 2/1999 |
| JP | 2000-224992 | 8/2000 |
| WO | WO 91/19717 A1 | 12/1991 |
| WO | WO 94/19351 A1 | 9/1994 |
| WO | WO 96/34867 | 11/1996 |
| WO | WO 97/35989 | 10/1997 |
| WO | WO 98/46606 A1 | 10/1998 |
| WO | WO 98/52568 A1 | 11/1998 |
| WO | WO 99/01439 | 1/1999 |
| WO | WO 99/19305 | 4/1999 |
| WO | WO 99/20273 | 4/1999 |
| WO | WO 00/17345 | 3/2000 |
| WO | WO 00/00197 | 6/2000 |
| WO | WO 01/00851 | 4/2001 |
| WO | WO 01/46145 | 6/2001 |
| WO | WO 01/56567 | 8/2001 |
| WO | WO 01/64200 | 9/2001 |
| WO | WO 01/77086 | 10/2001 |
| WO | WO 01/78721 | 10/2001 |
| WO | WO 01/85924 | 11/2001 |
| WO | WO 02/060428 A2 | 8/2002 |
| WO | WO 03/002567 A1 | 1/2003 |
| WO | WO 03/020702 A2 | 3/2003 |
| WO | WO 03/020724 A1 | 3/2003 |
| WO | WO 03/037432 A1 | 5/2003 |
| WO | WO 03/037899 A1 | 5/2003 |
| WO | WO 03/042216 A1 | 5/2003 |
| WO | WO 03/057165 | 7/2003 |
| WO | WO 2004/005281 | 1/2004 |
| WO | WO 2004/056831 A1 | 7/2004 |
| WO | WO 2004/087906 A1 | 10/2004 |
| WO | WO 2004/110452 | 12/2004 |
| WO | WO 2005/016962 | 2/2005 |
| WO | WO 2005/039586 | 5/2005 |
| WO | WO 2005/072826 | 8/2005 |
| WO | WO 2006/133261 A2 | 12/2006 |
| WO | WO 2007/025103 A2 | 3/2007 |
| WO | WO 2007/143705 A2 | 12/2007 |
| WO | WO 2008/057599 | 5/2008 |
| WO | WO 2008/063505 A1 | 5/2008 |
| WO | WO 2008/153959 | 12/2008 |
| WO | WO 2008/153974 | 12/2008 |
| WO | WO 2009/073210 A1 | 6/2009 |
| WO | WO 2009/075784 A1 | 6/2009 |

OTHER PUBLICATIONS

DeMattos, et al.,"Peripheral anti-Aβ Antibody Alters CNS and Plasma Aβ Clearance and Decreases Brain Aβ Burden in a Mouse Model of Alzheimer's Disease," PNAS (2001) 98(15): 8850-8855.

Dominguez et al., Secretases as therapeutic targets for the treatment of Alzheimer's disease, Amyloid: J. Protein Folding Disord. 8, 124-142(2001).

Dou, et al., "Chaperones Increase Association of the Tau Protein with Microtubules," Proc. Natl Acad Sci USA (2003) 100(2): 721-726-12449.

Dumont et al, Synthesis and Study of the Anti-Leukaemic Activity of N,N'-Substituted Amidines and Bis-Amidines, J. Pharm. Belg., 40:6, 373-386 (1985).

Durkin, et al, "Rank-Order of Potencies for Inhibition of the Secretion of Aβ340 and Aβ342 Suggests That Both Are Generated by a Single γ-Secretase," The Journal of Biological Chemistry (1999) 274(29): 20499-20504.

Esler, et al., "Transition-State Analogue Inhibitors of γ-Secretase Bind Directly to Presenilin-I ," Nature Cell Biology (2000) 2: 428-434.

Esler, W.P., et al. "A Portrait of Alzheimer Secretases—New Features and Familiar Faces," Science, 2001, pp. 1449-1454, vol. 293.

Gasparini, et al., "Stimulation of β-Amyloid Precursor Protein Trafficking by Insulin Reduces Intraneuronal β-Amyloid and Requires Mitogen-Activated Protein Kinase Signaling," The Journal of Neuroscience (2001) 21 (8): 2561-2570.

Gilman, S., et al. Clinical effects of Aβ Immunization (AN1792) in Patients with AD in an Interrupted Trial, Neurology, 2005, pp. 1553-1562, vol. 64.

Goodwin, et al., P3-215: "Inhibition of gamma-secretase activity induces cell cycle defects and chromosome missegregation", Alzheimer's & Dementia, vol. 4, No. I, p. T614 Jul. 1, 2008.

Jin, S.M., et al. "DNA damage inducing agents elicit γ-secretase activation mediated by oxidative stress." *Cell Death and Differentiation* 2008, vol. 15, p. 1375-1384.

Kraker et al., Biochemical and Cellular Effects of c-Src Kinase-Selective Pyrido[2,3-d]pyrimidine Tyrosine Kinase Inhibitors, Biochemical Pharmacology, vol. 60, pp. 885-898 (2000).

Moasser, et al., "Inhibition of Src Kinases by a Selective Tyrosine Kinase Inhibitor Causes Mitotic Arrest," Cancer Research (1999) 59: 6145-6152.

Nagar, et al., "Crystal Structures of the Kinase Domain of c-AbI in Complex with the Small Molecule Inhibitors PD173955 and Imatinib (STI-571)," Cancer Research (2002) 62: 4236-4243.

Petanceska, et al., The Phosphatidylinositol-3-Kinase Inhibitor Wortmannin Alters the Metabolism of the Alzheimer's Amyloid Precursor Protein, Journal of Neurochemistry (1999) 73(6): 2316-2320.

Schenk, D., et al. Immunization with Amyloid-β Attenuates Alzheimer-Disease-Like Pathology in the PDAPP Mouse, Nature, 1999, pp. 173-177, vol. 400.

Schindler, et al., "Structural Mechanism for STI-571 Inhibition of Abelson Tyrosine Kinase," Journal of Neurochemistry (2000) 289: 1938-1942.

Selkoe, D.J. Alzheimer's Disease: Genotypes, Phenotype, and Treatments, Science, 1997, p. 630, vol. 275.

(56) References Cited

OTHER PUBLICATIONS

Selkoe, Dennis J., "Deciphering the Genesis and Fate of Amyloid β-Protein Yields Novel Therapies for Alzheimer Disease," J Clin Invest 110: 1375-1381 (2002).
Tsao, P.-N., et al. "γ-secretase activation of Notch signaling regulates the balance of proximal and distal fates in progenitor cells of the developing lung." *J Biol Chem* 2008, vol. 283, p. 29532-29544.
Uniprot_A4D1B5, Gamma-secretase-activating protein, Protein pigeon homolog. Last modified Sep. 10, 2011 [online]. Retrieved Nov. 10, 2011 from the internet, http://www.uniprot.org/uniprot/A4D1B5.
Vandermeeren, et al., "The Functional -γ-Secretase Inhibitor Prevents Production of Amyloid β 1-34 in Human and Murine Cell Lines," Neuroscience Letters. (2001) 315: 145-148.
Vassar, R., et al. β-Secretase Cleavage of Alzheimer's Amyloid Precursor Protein by the Transmembrane Aspartic Protease BACE, Science, 1999, pp. 735-741, vol. 286.
Weisberg, et al. "Mechanisms of resistance to imatinib (ST1571) in preclinical models and in leukemia patients", Drug Resistance Updates, vol. 4, Issue 1, p. 22-28 (2001) Abstract Only.
Williamson et al., Rapid Tyrosine Phosphorylation of Neuronal Proteins Including Tau and Focal Adhesion Kinase in Response to Amyloid-β Peptide Exposure: Involvement of Src Family Protein Kinases, J. of Neuroscience, 22(1): 10-20 (Jan. 1, 2002).
Wolfe, M., γ-Secretase Inhibitors as Molecular Probes of Presenilin Function, J. Mol. Neuroscience, vol. 17, pp. 199-204 (2001).
Wolfe, Michael S., "Secretase Targets for Alzheimer's Disease: Identification and Therapeutic Potential," Journal of Medicinal Chemistry (2001) 44(13): 2039-2060.
Xu, et al., "Generation of Alzheimer β-Amyloid Protein in the Trans-Golgi Network in the Apparent Absence of Vesicle Formation," Proc. Natl. Acad. Sci (1997) 94: 3748-3752.
Zhang, et al., "Biochemical Characterization of the γ-Secretase Activity That Produces β-Amyloid Peptides," Biochemistry (2001) 40: 5049-5055.
Netzer, et al. *Proc Natl. Acad. Sci.*, 100(21), pp. 12444-12449, (2003).
Zimmermann, et al., *Bioorganic & Medicinal Chem. Lett.*, 7(2), pp. 187-192, (1997).
He, et al., *Nature*, 467(2), pp. 95-99, (2010).
Abel et al. *Cell* 88: 615-626, 1997.
Ahn et al. *J. Med. Chem*. 40: 2196-2210, 1997.
Allende et al, Comp Biochem Physiol (1987) 88(2):581-587.
Alvarez & Davis, "A Semi automated Method for the Assay of Cyclic Adenosine 5' -Monophosphate Phosphodiesterase," (1996), Analytical Biochemistry, 236: 367-369.
Bach, et al. *Cell* 81: 905-915, 1995.
Bastia et al, Neurosci Letters (2002) 328:241-244.
Bender et al, Pharrmacol Rev (2006) 58: 488-520.
Bibb et al., "Severe Deficiencies in Dopamine Signaling in Presymptomatic Huntington's Disease Mice," (2000), PNAS, 97:6809-6814.
Bönöczk et al., Role of sodium channel inhibition in neuroprotection: Effect of vinpocetine, Brain Research Bulletin, 2000, vol. 53, No. 3, pp. 245-254.
Borisy et al. *J. Neurosci*. 12: 915-923, 1992.
Bourtchuladze et al. *Cell* 79: 56-68, 1994—(Abstract only).
Burnouf et al., "Synthesis, Structure-Activity Relationships, and Pharmacological Profile of 9-Amino-4-Oxo-I-Phenyl-3,4,5,6,7-Tetrahydrol[I,4JDiazepino[6,7,I-hi]Indoles: Discovery of Potent, Selective Phosphodiesterase Type 4 Inhibitors," (2000), J. Med. Chem., 43: 4850-4867.
Chebib et al, Bioorg & Med Chem (2000) 8:2581-2590.
Chermat et al, Pharmacol (1986) 17:348-350.
Cummings, JL et al., "Metrifonate (Trichlorfon): a review of the pharmacology, pharmacokinetics and clinical experience with a new acetylcholinesterase inhibitor for Alzheimer's disease", Expert Opin Investig Drugs, 1999, vol. 8 (4), pp. 463-471 (doi:10.1517/13543784.8.4.463).

Davis et al. *Mol. Cell. Biochem*. 149/150: 271-278, 1995—(Abstract only).
Dewald et al, J Med Chem (1988) 31:454-461.
Dousa, Kidney Int 55: 29-62, 1999.
Du et al., "Minocycline Prevents Nigrostriatel Dopaminergic Neurodegeneration in the MPTP Model of Parkinson's Disease," (2001), PNAS, 98:14669-14674.
Duplantier et al., "7-Oxo-4,5,6,7-Tetrahydro-1H-Pyrazolo[3,4-c) Pyridines as Novel Inhibitors of Hyman Eosinophil Phosphodiesterase," (1998), J. Med. Chem., 41:2268-2277.
Ehrman et al., "Phosphodiesterase 1B differentially modulates the effects of methamphetamine on locomotor activity and spatial learning through DARPP32-dependent pathways: evidence from PDE1B-DARPP32 double-knockout mice", Genes Brain Behav. Oct. 2006; 5(7):540-51.
Elvevag et al, Critical Reviews in Neurobiology (2000) 14(1):1-21 (abstract only).
Erneux et al., "A Mechanism in the Control of Intracellular cAMP Level: The Activation of a Calmodulin-Sensitive Phosphodiesterase by a Rise of Intracellular Free Clacium," (1985), Molecular and Cellular Endocrinology, 43: 123-134.
Escalera et al. *Endo*. 131 (6): 2965-2971, 1992.
Esfahani et al, Iranian J of Pharmacol and Therapeutics (2002) 1:8-11.
Fienberg et al. *Brain Research* 31(2-3): 313-319, 2000.
Fienberg et al., "DARPP-32: Regulator of the Efficacy of Dopaminergic Neurotransmission," (1998), Science, 281: 838-842.
Furuyama et al. *Mol. Brain Res*. 26: 331-336, 1994—(Abstract only).
Gally et al. *Proc. Natl. Acad. Sci. USA* 87: 3547-3551, 1990.
Garthwaite, *J. Trends Neurosci*. 14: 60-67, 1991—(Abstract only).
Goldman-Rakic et al, Psychopharmacology (2004) 174:3-16.
Greengard et al. Neuron 23: 435-447, 1999.
Guzowski et al. *Proc. Natl. Acad. Sci. USA* 94: 2693-2698, 1997.
Hamilton, et al., "Synthesis and Structure-Activity Relationships of Pyrazoloú4,3-d 3/4 Pyrimidin-7-Ones as Adenosine Receptor Antagonists" *Journal of Medicinal Chemistry, American Chemical Society*, Washington, US, vol. 30, No. 1, pp. 91-96 (1987).
Han, P. et al., "The Calcium/Calmodulin-Dependent Phosphodiesterase PDE1C Down-Regulates Glucose-Induced Insulin Secretion", The Journal of Biomedical Chemistry, vol. 274, No. 32, (1999), pp. 22337-22341.
Hebb et al. Neuroscience 123: 967-981,2004.
Houslay et al, "The Multienzyme PDE4 Cyclic Adenosine Monophosphate-Specific Phosphodiesterase Family: Intracellular Targeting, Regulation, and Selective Inhibition by Compounds Exerting Anti-Inflammatory and Antidepressant Actions," (1998), Advances in Pharmacology, 44:225-342.
Jaber et al. *Neuropharmacology* 35: 1503-1519, 1996.
Jassen et al. *Mol. Pharmacol*. 70: 71-77, 2006.
Kakkar et al. *Cellular and Molecular Life Sciences*, 55: 1164-1186, 1999.
Kotter, R. *Prog. Neurobiol*. 44: 163-196, 1994—(Abstract only).
Kruuse, et al., "Phosphodiesterase 5 and effects of sildenafil on cerebral arteries of man and guinea pig" *European Journal of Pharmacology*, Elsevier BV, NL, vol. 521, No. 1-3, 3, pp. 105-114 (Oct. 2005).
Lincoln, Molecular Pharmacol (2004) 66:11-13.
Lindskog et al. *Neuroscience* 88: 1005-1008, 1999.
Livingstone et al. *Cell* 37: 205-215, 1984.
Lundqvist et al, Nature (2007) 447:817-822.
Mani et al, Science (1994) 265:1246-1249.
Mani et al, Science (2000) 287:1053-1056.
Mansuy et al. *Cell* 92: 39-49, 1998.
Mayerhofer, et al. *J. Clin. Endocrin. Metab*. 84(1): 257-265, 1999.
Mayford et al. *Cell* 81: 891-904, 1995.
Morissette et al, Advanced Drug Delivery Reviews (2004) 56:275-300.
Murray et al, JPET (2003) 306:752-762.
Nishi et al., Bidirectional Regulation of DARPP-32 Phosphorylation by Dopamine, (1997), The Journal of Neuroscience, 17: 8147-8155.
Polli & Kincaid. *J. Neurosci*. 14: 1251-1261, 1994.

(56) References Cited

OTHER PUBLICATIONS

Porsolt et al, Nature (1977) 266:730-732.
Poulsen et al, Bioorg & Med Chem Letter (2001) 11:191-193.
Puckett et al., "Molecular Cloning and Chromosomal Localization of one of the Human Glutamate Receptor Genes," (1997), PNAS, 88:7557-7561.
Qiu & Davis. *Genes* Dev. 7: 1447-1458, 1993.
Reed et al. Jour of Neurosci 22: 5188-5197, 2002.
Repaske et al., A Polymerase Chain Reaction Strategy to Identify and Clone Cyclic Nucleotide Phosphodiesterase cDNAs: (1992), The Journal of Biological Chemistry, 267:18683-18688.
Rozic, J. et al., "Cyclooxygenase inhibitors retard murine mammary tumor progression by reducing tumor cell migration, invasiveness and angiogenesis", Int. J. Cancer, 2001; vol. 93 (4); pp. 497-506.
Rybalkin et al, Circ Res (2003) 93:280-291.
Sakakibara et al. *Neuroendo*. 68: 365-373, 1998.
Sharma et al. *J. of Biological Chemistry* 255: 5916-5923, 1979.
Shimizu, K. et al., "Calmodulin-Dependent Cyclic Nucleotide Phosphodiesterase (PDE1) is a Pharmalogical arget of Differentiation-Inducing Factor-1, an Antitumor Agent Isolated from Dictyostelium", Cancer Res., (Apr. 1, 2004), vol. 64, No. 7, pp. 2568-2571.
Skoulakis, et al. *Neuron*. 11: 197-208, 1993—(Abstract only).
Snyder et al. *J. Neurochem*. 63: 1766-1771, 1994.
Svenningsson et al. *Neuroscience* 84(1): 223-228, 1998.
Svenningsson et al. The AAPS Jour. 7: E353-E360, 2005.
Traficante et al., "Dopamine-Sensitive Adenylate Cyclase and cAMP Phosphodiesterase in Substantia Nigra and Corpus Striatum of Rat Brain," (1976), Life Sciences, 19: 1061-1066.
Tsou et al., Nitric oxide/cGMP pathway stimulates phosphorylation of DARPP-32, a dopamine- and cAMP-regulated phosphoprotein, in the substantia nigra, Proc. Natl. Acad. Sci USA, Apr. 1993, vol. 90, pp. 3462-3465.
Turko et al, Mol Pharmacol (1999) 56:124-130.
Uckert et al, J Urology (2004) 171(4):428 (abstract).
Ungerstedt , Acta Physiol Scand Suppl (1971) 367:1-48.
Ungerstedt et al., Brain (1970) 24:485-493.
Vatter, S. et al., "Differential Phosphodiesterase Expression and Cytosolic $Ca^{2+}$ in Human CNS Tumour Cells and in Non-Malignant and Malignant Cells of Rat Origin", Journal of Neurochemistry, (2005), vol. 93, pp. 321-329.
Vippagunta et al, Advanced Drug Delivery Reviews (2001) 48:3-26.
Weisburger, JH. "Antimutagens, anticarcinogens, and effective worldwide cancer prevention", J Environ Pathol Toxicol Oncol, 1999; vol. 18 (2), pp. 85-93.
Xia, et al., J Med Chem (1997) 40:4372-4377.
Yan et al. *J. Biol. Chem*. 271: 25699-25706, 1996.
Yan et al. *J. Neurosci*. 14: 973-984, 1994.
Yan et al. *Proc. Natl. Acad. Sci. USA*. 92: 9677-9681, 1995.
Yin et al. *Cell* 79: 49-58, 1994—(Abstract only).
Francis, et al., *Developmental Cell*. (2002) 3(1): 85-97.
Iwatsubo, T., et al., *Neuron* (1994) 13:45-53.
Langman et al., *Lancet*. (1994) 343: 1075-1078.
Li et al., *J. Neurochem*. (2002) 82(6): 1540-1548.
Mann, et al., *Am. J. Pathol*. (1996) 148: 1257.
Roher et al., *Proc. Natl. Acad. Sci. USA*. (1993) 90: 10836-10840.
Steiner et al., *J. Biol. Chemistry*. (2002) 277(42): 39062-39065.
Yamaguchi et al., *Amyloid Int. J. Clin. Invest*. (1995) 2: 7-16 (Abstract Only).
International Search Report for International Application No. PCT/US03/00249 mailed Jul. 30, 2003.
Cai J X et al: "Dose-dependent effects of the dopamine D1 receptor agonists A77636 or SKF81297 on spatial working memory in aged monkeys", *J. Pharma. Exp. Therap.*, vol. 283 (1), p. 183-189 (1997).
RecName: Full=Gamma-secretase-activating protein; Short=GSAP; AltName: Full=Protein pigeon homolog; Contains: RecName: Full=Gamma-secretase-activating protein 16 kDa C-teminal form; Short=GSAP-16K, document states: created: May 20, 2008, sequence updated: May 20, 2008, annotation updated: Jul. 28, 2009; 4 pages; obtained from http://www.ncbi.nlm.nih.gov/protein/189041192?sat=12&satkey=1918148 on Aug. 19, 2016.
Uncharacterized protein LOC392943 homolog, document states: created: May 20, 2008, sequence updated Oct. 11, 2005, annotation updated: Jun. 10, 2008; 3 pages; obtained from http://www.ncbi.nlm.nih.gov/protein/123793106?sat=11&satkey=7563622 on Aug. 19, 2016.

\* cited by examiner

Figure 1A

| | |
|---|---|
| Homo | ----------------------------------------------------------MALRLVADEDLGKDVLPWLRA |
| Canis | ------------------------------------------------------------MTQNLSWPGH |
| Bos | -----------------------------------------------------MALRLIADFDLEKDVLPWLRV |
| Mus | ------------------------------------------------------MALRLVTHFDVLEDVLPSLLT |
| Rattus | ------------------------------------------------------MALRLVTHFDVLADVLPSLIV |
| Gallus | MAVAAPQQPARCGGQRPPECGRVGPRLRALPSGGRRSQAGRESPRAAHGAASPLLPSGPG |
| | |
| Homo | QRAVSEASGAGSG------------------------------GADVLENDYES--- |
| Canis | SSNGSCIRFPVAG------------------------------GTAVL------- |
| Bos | QLAASAAAGARGG------------------------------GPGVLENNYEC--- |
| Mus | QAATDEGDRAGV------------------------------LETTYG------S--- |
| Rattus | QAATADEGDEGA------------------------------ETTLG------S--- |
| Gallus | RLEATGGRGNGGGASGRPQLRGLSPEAPLPCGGCAGPELRGLTLSLCGGSALDTSEKSSA |
| | |
| Homo | LHVLNVERNGNIIYTYKDDKGNVVFGLYDCQTRQNELLYTFEKDLQVFSCSVNSERTLLA |
| Canis | ------WQGAVSSIQGLGTADHELPTWRAYEQLPYADLA |
| Bos | LRVLNVERNRNIIYTYKDNKGNVFFGLYDYQTRQNEHLYTFEKDLQVVSCSVNKERTLLA |
| Mus | LRVLNIERNGNIIYTYKDNKGNAVFGLYDCQTRQNEHLYTFEKDMQAVSCSVNSERTVLA |
| Rattus | LRVLNIERNGDIIYTYKDNKGNAVFGIFDCQTRENEHLYTFEKDMQAVSCSVNSERTVLA |
| Gallus | LYIVNVERNGKIIYTWKGMQRSTHIGLYDLQTKENEHLYTFEKDIRIISCSVNSERTLLA |
| | |
| Homo | ASLVQSTK-EGKRNELQPGSKCLTLLVEIHPVNNVKVLKAVDSYIWVQFLYPHLESHPLP |
| Canis | SVDLCIQL-LIPFAFIPTGSKCLTLLVEIHPVNNVKVLKAVDSSIWVQFLYPQVESHPPP |
| Bos | TSLVQAAK-EGRSNELQPGSKCLTLLVEIHPVNNVKVLKAVDSYIWVQFLYPHVESCPQP |
| Mus | ASFIQYT-EGVKNDLQPGSKCLTLLVEIHPVNNVKVLKAVDSCVWVQFLYPQAFSHLLP |
| Rattus | ASFIQYT-EGVRSELQPGSKCLTLLVEIHPVNNVTVLKAVDSCVWVQFLYPQAFSHLLA |
| Gallus | VSFRQYTEEERVTHLLQSVSKYLALLIEIHPVNNVKVLKAVDSCVRVQFLYPVEDRNSST |
| | |
| Homo | ENHLLLISEEKYIEQFRIHVAQEDGNAVVIKNSGHLPRDRIAEDFVWAQWDMSEQRLYYI |
| Canis | EMHLLLISEEKYIEKFHIHVIQEDGNAKVLRDSGHLPRERVAEDFVWAQWDMSEQRLYYI |
| Bos | KNHLLLLSEEKYIEQFHIQVVQEDGNRVVIKNSGHLPRERIAEDFVWAQWDMSEQRLYYI |
| Mus | QNHLLLISEEKYIERFHIQITTREDGDRVVIRNSSHLPRDRLAEDFVWAQWDLSEQRLYYI |
| Rattus | QNHLLLISEEKYIERFHIQITTREDGNRVVIRNSSHLPRERIAEDFVWAQWDVSEQRIYYI |
| Gallus | ESHLLLVSEDKYIEQFDIHVAEEE--HRVVIQNSGQLPRARVADLIWAQWDMTEQRLFYI |

Figure 1B

| | |
|---|---|
| Homo | DLKKSRSILKCIQFYADESYNLMFEVPLDISLNSGFKLVNFGCDYHQYRDKFSKHLTLC |
| Canis | VLKKSRSILKCIQFSANEKFNLMFEAPLDITLSASGFELVNFGCDDLQDQGNLSKHLTLC |
| Bos | DLKKSRSVLKCIQFYAEEHFNLMFEAPLDISLSDSGFKLVNFGYSDLQDKEELSEHLTLC |
| Mus | ELKESRSILKCIQFRADESFNLMFEMPLDITLTGLRFKLVNFGYDYRQDREKLCNQPSLC |
| Rattus | ELQESRSILKCVQFWADESFTIMFEMPLDISLSGLRFKLVNFGYDYRQDQAKLCHQPSLC |
| Gallus | VPKESRSILRCVQFYPDENFNSTLESQLDISVNDKRVKLVNFGYNDCEDRDVPPKSLNLQ |
| | |
| Homo | VFTNHTGSLCVCYSPKCASWGQITYSVFYIHKGHSKTFTTSLENVGSHMTKG———————— |
| Canis | VFTNHTGSLCVCYSPKFDSWEKITYSVFYFHKGHSKTFTAALGSVDSLVTKG———————— |
| Bos | VFTNHTGSLCVCYCPNFDSWEQITYSVFYFHKGHSKTFTTTLGSVDSHVTKG———————— |
| Mus | IFTNHTGSLCMCYSPKSDSREEITYSVFYLHKGYRKIFTAAPGSADSQVTNGADSQVTDG |
| Rattus | IFTNHTGSLCVCYSPKSDSWKEITYSVFYLHKGYRKTFTVAPGSTDSQVANG———————— |
| Gallus | VFTNKAG——————————————————————————————FSKTFTASLERPETPQLKE———— |
| | |
| Homo | ITFLNLDYYVAVLPGHFFHLLNVQHPDLICHNLFLTGNNEMIDMLPHCPLQSLSGSLVL |
| Canis | LTFLNLDYYVAVLPGHFFHLLNIQHPDLICHSLFLTGNNEVVDMLPHSPLQSLSGSLVL |
| Bos | ITFLNLDYYVAVLPGHFFHLLNIQHPDLICHSLFLTENSEVIDMLPHSPLQSLSGSLVL |
| Mus | IAFLNLGYFVAVYSPGHFLHLLNIQHPDLVCHSLFLTGNNKIAAVLPPSPLQSLPGSLVL |
| Rattus | VTFLNLGYFVAVYSPCRFLHLLNIRHPDLICHSLFLTGNNKTAAVLPPSPLQSLPGSLIL |
| Gallus | VAFLNLDYYVAAYLPGQFLHLLNIQHPDLLCYSLFLTGEDARIDMLPNCSIQSPLVSTVL |
| | |
| Homo | DCCSGKLYRALLSQSSLIQLLQNTCLDCEKMAALHCALYCGQGAQFLEAQIIQWISENVS |
| Canis | DWCSGKLYRALLNQSYLLQFLWNTQLDCEKMAVLHCVLSCGRDPRFLEAKIIQWISENIS |
| Bos | DSRSGKLYRVLLNQSYLVEFLRSARLDCERMALLHCALSHGRDPRRLEAKIIQWISENIS |
| Mus | DCYSGKVYRVTLDQSYLLRFLWNAHLDCERMAALHCILSCSQDPGFPEEQIIQWISEHVS |
| Rattus | DCSSGKVYRATLDQSYLMGFLWNAQLDCEKMAALHCALSCDSDPGFPE-QIVQWSERVS |
| Gallus | DCCIGRLYAMSISDSALIKYLQNSKRDSERLAALHCALLCVRRTTDLEMKITWWISENLS |
| | |
| Homo | ACHSFDLIQEFIIASSYWSVYSETSNMDKLLPHSSVLTWNTEIPGITLVTEDIALPLMKV |
| Canis | TCHSFDLIQEFIIASSYWSIYPETSNIDKLLPYSSVLTWNTEIPGITLVTEEITTLPFMKV |
| Bos | ACHSFDLIQEFIIASSYWSIYPETSNMDKLLPYSSLLTWDTEIPGITLVTEEIPLPLMKV |
| Mus | ACHSFDLIQEFLIASSYWSVVAELDDMGMLLQYSSVLTWNTEIPGIKFTEELPLPLMKV |
| Rattus | ACHSFDLIQEFLIASSYWSVYPGLDDVDLLLPYSSVLTWDTEIPGMKLVTEELPLPLMKV |
| Gallus | TCHSFDPIQEFIIASLYCRMCPETNNLDKLLPYTSLLDWTGVIPGVACATDIISLPVLEM |

Figure 1C

```
Homo    LSFKGYWEKLNSNLEYVKYAKPHFHYNNSVVRREWHNLISEEKTGKRRSAAYVRNILDNA
Canis   HSFKGYWEKLNSNLEYVKCSKPCLLYNNSMVKREWHSLISEEKTGRRRSMVYVRNIFDNA
Bos     HSFKGYWEKLNSNLEYVKYSKPHLHYNNSVVRREWHNLISEEKTGKRRSTVYVRNILDNA
Mus     YGLKGYWAKLNSNLEYIKYTKPHLHYHNSVVRREWHNLISEERTGKRRSTMYVRNILENA
Rattus  YSLKGYWAKLNSNLEYIKYTKPHLHYHNSVVRREWHNLISEERTGKRRSTMYVRNILDNA
Gallus  QNSKGFWEKLDSNLESVKYAEPHLHYHNNVLRREWRNLSEE-------------------

Homo    VKVISNLEARNLGPRLTPLLQEEDSHQRLIMGIMVSELKDHFLRHLQGVEKKKIEQMVLD
Canis   MKVISNLEARNLEPRLTPLFQEEDYHQRLLIGIMVSELREHLLRHLQGIGKKKIEQMVLD
Bos     IKVISNVEAKNLEPRLTPLFQEEDTHQQLLIGIMVSELREHLLRHLQGVEKRKIEQMVLD
Mus     MKVIASMETRTLEPRLIPFLQEEDRHQRLIMGIMVSELRDHLLRHLQGVEKAKIEQMVLD
Rattus  VKVISNMEMKTFEPRLIPLLQEEDRHQRLIMGIMVSELRDHLLRHLQGVEKAKIEQMVLD
Gallus  --------------------------MVAQLKDHLMRHLQYVGKKKIDQIVLD Homo    YISKLLDLICHIVETNWRKHNLHSWVLHFNSRGSAAEFAVFHIMTRILEATNSLFLPLPP
Canis   YISKLLDLICQILETSWRTHHLHPWVLHL--RASAAEFTVFHIMTRILFATMSLFLPLPP
Bos     YVSKLLDLICQILEASWRKHNLHPWALHFNRQASAAEFAVFHIMTRILEATNTLFLPLPP
Mus     YISKLLDLIWCLLETSWRKHSMHPLVLHLNSHCSAADFEVFHLMTRILDAASSLCLPLPP
Rattus  YISKLLDLIWCLLETSWRKHSVHPWVLHLNEHGSPADFEVFHLMTRILDAASSLCFPLPP
Gallus  YVANLLNLVHRIMKEVWKIHQLHSCIFCFDERGSEAEFRVFHIMSRILEAANGMCMPLPP Homo    GFHTLHTILGVQCLPLHNLLHCIDSGVLLLTETAVIRLMKDLDNTEKNELKFSIIVRLP
Canis   GFHTLHTILGVHCLPLHNLLHYIDSGVLLLTETAVIRLMKDLDNSENNEKLKFSIIVRLP
Bos     GFHTLHMILGVRCLPLHNLLHYIDHGVLLLTEAAVTRLMKDLDNTEKNEKLKFSIMRLP
Mus     GFHSLHTILGVHCLPLYSLLHYIDNGVLLLTETAVTRLMKDLDNSEKNEQLKFSIIVRLP
Rattus  GFHSLHTILGVHCLPLYNLLHYIDNGVLLLTETVVTRLMKDLDNSEKNEKLKFSIIVRLP
Gallus  GFHSLHLGLGVRCLPLHTLLHYIDNGVLHLTETCVRKLIKDLDDNEKNEKLKFSIVTRLP Homo    PL-----IGQKICRLWDHPMSSNIISRNHVTRLLQNY-KKQPRNSMINKSSFSVEFLPLNY
Canis   PH------IGQKICRLWDHPMSSNIISRNHVKQLLLNY-KKQPQSSMIDKSPGSVEFLPLNY
Bos     PL-----TGQKICRIWDHPVSSNIISRNHVKRLLQNY-NKQPWSSVMDKSSFSVEFLPLNY
Mus     PL-----IGQKVCRLWDHPMSSNIISRNHVARLLKNY-RKEPRNSMIDKSSFPVEFLPLNY
Rattus  PL-----IGQKVCRLWDHPMSSNIISRNHVAQLLKNY-KKEPQSSMIDKSSFPVEFLPLNY
Gallus  EVTLDALGLKARQFWDHPVNANFRARKYVKLLLEKLGNRQCSRPVPERHPVCVEFLPLNY
```

Figure 1D

```
Homo    FIEILTDIESSNQALYPFEGHDNVDAEFVEEAALKHTAMLLGL----
Canis   FIEILTDIESSNQALYAFEGHDNVDAKFVEEAALKHTTMLLGL----
Bos     FIHILTDIESSNPALYAFEGHDNVDAKFVEEAALKHTAMLLGL----
Mus     FIEILMGLESSNQALYGFEGHDNVDAEFVEEAALKHTTMLLGL----
Rattus  FIEILMHLESSNQALHGFEGHDNVDAEFVEEAALKHTTSLLGL----
Gallus  LTNVLAEIES--QGVHLYEKQDHINVRFVEEAALKHTMMLLGLRYS
```

REGULATORY PROTEINS AND INHIBITORS

CROSS REFERENCE TO RELATED APPLICATIONS

This application is a continuation of PCT/US2010/002173 filed on Aug. 5, 2010, which claims the benefit of U.S. Provisional Application No. 61/231,462, filed Aug. 5, 2009, the contents of each of which are incorporated herein by reference.

TECHNICAL FIELD

The field relates to a previously uncharacterized protein that activates γ-secretase to produce β-amyloid protein (Aβ). Deposition of Aβ has been associated with Alzheimer's disease and other pathologies. The invention provides, e.g., screening methods and novel research tools, inhibitors of this novel protein, and methods of treatment and control of Alzheimer's disease and other neurodegenerative conditions associated with deposition of Aβ.

BACKGROUND OF THE INVENTION

Currently, over twelve million people worldwide suffer from Alzheimer's Disease (AD). This number is predicted to quadruple over the next 40 years. As such, treatment of AD represents a major unmet medical need. Currently approved medicines to treat AD may help ameliorate symptoms, but are not effective to stop progression of the disease.

Without being bound by a particular theory, it is believed that the pathology of Alzheimer's disease ("AD") involves amyloid-β ("Aβ") peptides, which are metabolites of β-amyloid precursor protein (Alzheimer's disease-associated precursor protein or "APP"), and are believed to be major pathological determinants of AD. These peptides exist mainly in 40 or 42 amino acid forms, Aβ1-40 ("Aβ40") and Aβ1-42 ("Aβ42"), respectively. Aβ40 and Aβ42 are generated by two enzymatic cleavages occurring close to the C-terminus of APP, subsequent to cleavage by beta secretase. The enzymes responsible for the cleavage, β-secretase and γ-secretase, generate the N- and C-termini of Aβ, respectively. The amino terminus of Aβ is formed by β-secretase cleavage between methionine residue 596 and aspartate residue 597 of APP (numbering based on APP 695 isoform). γ-secretase cleaves at varying positions 38-, 40- or 42-residues at the C-terminal of this β-secretase cleavage product to release the Aβ peptides. A third enzyme, α-secretase, cleaves the precursor protein between the β- and γ-cleavage sites, thus precluding Aβ production and releasing an approximately 3 kDa peptide known as P3, which is non-pathological. Both β- and α-secretase cleavage also result in soluble, secreted-terminal fragments of APP, known as sAPPβ and sAPPα, respectively. The sAPPα fragment has been suggested to be neuroprotective. For example, γ-secretase also cleaves Notch-1 protein and is believed to have other substrates. Direct acting gamma-secretase inhibitors have substantial and unwanted side effects due to the effects on development pathways requiring Notch cleavage. Little is known about the molecular mechanisms that confer substrate specificity on this potentially promiscuous enzyme. Gamma secretase enzyme is known to contain four subunits: presenilin, nicastrin, anterior pharynx-defective 1 (APH-1), and presenilin enhancer 2 (PEN-2).

In normal individuals, the Aβ peptide is found in two predominant forms, the majority Aβ-40 (also known as Aβ1-40) form and the minority Aβ42 (also known as Aβ1-42) form, each having a distinct COOH-terminus. The major histological lesions of AD are neuritic plaques and neurofibrillary tangles occurring in affected brain regions. Neuritic plaques consist of Aβ peptides, primarily Aβ40 and Aβ42. Although healthy neurons produce at least ten times more Aβ40 compared to Aβ42, plaques contain a larger proportion of the less soluble Aβ42. Patients with the most common form of familial Alzheimer's disease show an increase in the amount of the Aβ42 form. The Aβ40 form is not associated with early deposits of amyloid plaques. In contrast, the Aβ42 form accumulates early and predominantly in the parenchymal plaques and there is strong evidence that Aβ42 plays a major role in amyloid plaque deposits in familial Alzheimer's disease patients. Neurofibrillary tangles consist of aggregated tau protein and their role in AD pathology is less clear. AD symptoms are most closely correlated with total brain Aβ rather than plaques. About 10% of AD cases result from autosomal dominant inheritance of mutations in either the APP or the presenilin 1 and presenilin 2 genes. In both cases, increased production of total Aβ or Aβ42 versus Aβ40 results.

The N2a cell system has been extensively studied as a model system of Aβ production relevant to neurodegeneration in AD. Assays measuring production of Aβ in N2a cells are known, wherein Aβ-production activity is evaluated e.g., by Aβ ELISA assay and/or by Western blotting. Various agents including compounds such as Gleevec (Imatinib, STI571) have previously been shown to be capable of lowering Aβ levels in the N2a cell system at drug concentrations of below 10 μM.

International Patent Publication No. WO 03/057165 discloses that certain previously known inhibitors of tyrosine kinases, such as imatinib, are useful to inhibit the production of and accumulation of Aβ. Netzer et al., *Proc Natl Acad Sci.*, 100(21):12444-9 (2003) showed that imatinib inhibits production of Aβ without affecting γ-secretase cleavage of Notch-1 and without unacceptable toxicity to the neurons. Imatinib is not an ideal drug for treating AD, however, because it does not penetrate the blood brain barrier very well, and it has other biological effects. The specific target of imatinib for inhibition of production of and accumulation of Aβ has not been defined, so finding improved derivatives presents challenges.

SUMMARY OF THE INVENTION

We have discovered a novel γ-secretase activating protein (gSAP) that selectively modulates Aβ production through a mechanism involving its interactions with both γ-secretase and its substrate, amyloid precursor protein C-terminal fragment (APP-CTF). gSAP does not interact with Notch nor affect its cleavage by γ-secretase. Recombinant gSAP stimulates Aβ production in vitro and in intact cells. Reducing gSAP in cell lines decreases Aβ levels. Knockdown of gSAP in mouse models of Alzheimer's disease reduces levels of Aβ and plaque development. gSAP represents a novel therapeutic target for the treatment of Alzheimer's disease and other Aβ-mediated conditions, as inhibition of gSAP results in significant reduction in Aβ formation.

Applicants have synthesized compounds that inhibit the gSAP and thus lead to decreased Aβ, but do not affect NOTCH metabolism, which is a potential side effect with use of some gamma-secretase inhibitors.

Accordingly, the invention provides, e.g., methods of screening compounds for potential utility in reducing Aβ comprising measuring their ability to selectively inhibit gSAP, and methods of treating Aβ-mediated conditions, such as AD, comprising administering effective amounts of a compound which selectively inhibit gSAP.

DESCRIPTION OF DRAWINGS

FIG. 1 depicts a sequence alignment for gSAP from various animal species: human, canine, bovine, murine, rat, and chicken. Residues in bold are identical across the six species; residues in italics are conservatively substituted.

DETAILED DESCRIPTION

Figure 2:
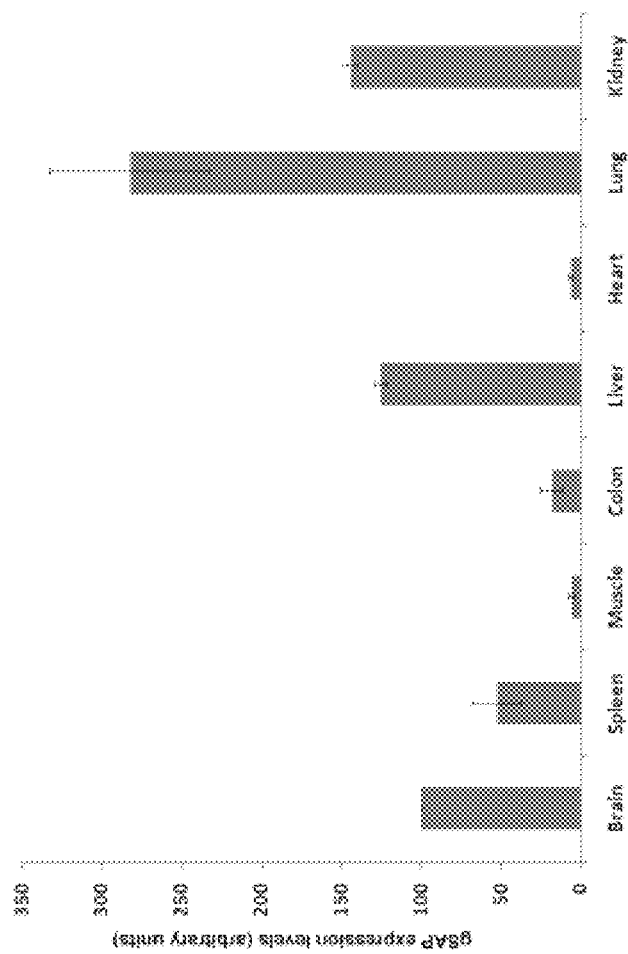
FIG. 2 depicts expression levels of gSAP in different tissues. Tissues from 3 month old wild type BL/6 mice are harvested and gSAP levels are quantitated using real time PCR. Both actin and GAPDH serve as internal controls (n=6). Tissue extracts are adjusted to the same protein levels prior to analysis.

The examples and drawings provided in the detailed description are merely examples, which should not be used to limit the scope of the claims in any claim construction or interpretation.

Senile plaques composed predominantly of Aβ peptides are a hallmark of Alzheimer's disease. Aβ is derived from APP-CTF upon cleavage by γ-secretase. γ-Secretase also cleaves many other type I membrane proteins (such as Notch), leading to the release of intracellular domains with critical cellular functions. As a result, non-selective γ-secretase inhibitors may have detrimental side effects that prevent their clinical use. This laboratory previously demonstrated that imatinib (STI571, Gleevec®) can inhibit production of all species of Aβ without influencing Notch cleavage. Netzer et al., *Proc Natl Acad Sci.*, 100(21):12444-9 (2003). We have now determined that the Aβ-lowering activity of imatinib results from its interaction with a previously unknown factor, which we designate γ-secretase activating protein (gSAP).

To identify the target responsible for imatinib's selective Aβ-lowering activity, we synthesized a biotinylated derivative of imatinib, "biotin-imatinib". Solubilized γ-secretase components, including presenilin-1, PEN2, and nicastrin, are specifically captured by the immobilized biotin-imatinib. To identify the protein with which imatinib directly interacts, we synthesized a photoactivatable azido imatinib derivative, G01. When $^{125}$I-G01 is incubated with a membrane preparation followed by photolysis, none of the four components of γ-secretase are labeled. Rather, $^{125}$I-G01 labels a ~16 kDa protein, which co-immunoprecipitates with the more slowly migrating 18 kDa presenilin-1-CTF. This result is confirmed by intact cell photolabeling using cell permeable $^{3}$H-G01. Similar to $^{125}$I-G01, the $^{3}$H-imatinib derivative does not bind to any of the four γ-secretase components, but does label a band of ~16 kDa that co-immunoprecipitated with PS1.

To purify the potential target protein, immobilized biotin-imatinib is incubated with solubilized membrane preparations and bound proteins are separated by SDS-PAGE. After silver staining, a ~16 kDa band is observed. Peptide fragments, derived from this band after trypsin digestion, and analyzed by tandem mass spectrometry, corresponded to the C-terminal region of an uncharacterized protein, pigeon homologue protein (PION) (human accession number: NP_059135). The identification is made based on two unique tryptic peptides ($^{766}$LWDHPMSSNIISR$^{778}$ and $^{779}$NHVTRLLQNYKK$^{790}$) covering approximately 20% of the 16 KDa fragment. Its sequence, especially the C-terminal region, is highly conserved among multiple species from chicken to human. Expression pattern analysis indicates that this gene is expressed in diverse tissues. We characterize PION as a gamma-secretase activating protein (gSAP).

Based on its predicted sequence, the full opening reading frame of human gSAP encodes a protein of 854 amino acids (~98 kDa). To determine whether the 16 kDa fragment might be derived from a high molecular weight precursor, the metabolism of endogenous gSAP in neuroblastoma cells is monitored by pulse-chase analysis. The results showed that gSAP is synthesized as a holo-protein (~98 kDa) and is rapidly processed into a ~16 kDa C-terminal fragment (gSAP-16K). In the steady state, the 16 kDa fragment is the predominant form. Incubation of neuroblastoma cells with photoactivatable $^{3}$H-G01 followed by immunoprecipitation with anti-gSAP antibody confirms that imatinib directly binds gSAP-16K. In presenilin 1/2 (−/−) embryonic stem cells, imatinib also binds gSAP, indicating that its binding to gSAP does not require presenilins. When gSAP levels are reduced using siRNA, the amount of γ-secretase associated with biotin-imatinib decreases significantly. This indicates that the affinity of imatinib for the γ-secretase complex depends on gSAP.

When siRNA is used to reduce gSAP level (by 72±15%) in neuroblastoma cells overexpressing APP695, the level of Aβ decreases about 50%. The addition of imatinib has little or no additional effect on Aβ levels. ShRNA-mediated gSAP knockdown (by 65±12%) in HEK293 cells expressing APP Swedish mutation also results in a decrease of Aβ40 and Aβ42 levels of 61% and 48%, respectively. Conversely, overexpression of gSAP in HEK293 cells expressing the APP Swedish mutation stimulates Aβ production by approximately 38%; the increase is abolished by imatinib treatment. Together, these findings indicate that gSAP is the molecule through which imatinib and related molecules lower Aβ.

One distinctive feature of imatinib is its selective inhibition of Aβ production while sparing Notch cleavage (Netzer et al., 2003). The effect of gSAP on Notch cleavage is evaluated using HEK293 cells stably expressing Notch ΔE (Notch without its extracellular domain), the Notch substrate for γ-secretase. The level of the γ-secretase cleavage product, the Notch intracellular domain (NICD), is not changed either by reducing gSAP levels using shRNA or by overexpressing gSAP. Thus, gSAP modulates the γ-secretase cleavage of APP, but not of Notch.

To further test whether gSAP can modulate γ-secretase activity, the effect of purified gSAP on Aβ production is examined in an in vitro γ-secretase assay. When recombinant gSAP-16K (aa 733-854 of full length human gSAP), isolated after expression in E. coli, is added to membrane preparations from HEK293 cells containing overexpressed APP-β-CTF, Aβ production is stimulated 2.4±0.3 fold. These in vitro results suggest that gSAP stimulates Aβ production by direct regulation of γ-secretase activity.

To determine whether endogenous gSAP might be in a complex with γ-secretase, we use gel filtration analysis of membrane proteins from neuroblastoma cells solubilized in 1% CHAPSO. Endogenous gSAP-16K and γ-secretase co-migrate as a high molecular weight complex. In addition, endogenous gSAP co-immunoprecipitates with γ-secretase components, providing further evidence that these proteins exist in a complex in cells. These results, together with those from the in vitro γ-secretase activity assay, strongly suggest that gSAP-16K is in a complex with γ-secretase and can activate the protease.

In contrast to some other regulators of γ-secretase activity, gSAP is selective and influences cleavage of APP but not of Notch. Although the mechanism of substrate selection by γ-secretase remains unclear, a number of other proteases and phosphatases with broad substrate recognition can achieve specificity through auxiliary factors that couple the core enzyme to a subset of substrates. To determine the mechanism by which gSAP might confer such specificity, we analyze its binding to specific substrates in HEK293 cells. gSAP-16K immunoprecipitates with APP-CTF but not with Notch ΔE. Addition of imatinib (10 μM) reduces the interaction between gSAP and APP-CTF by 47±14% (n=3). The binding of gSAP to APP-CTF, but not to Notch, may account for the selective effect of gSAP on APP processing. Disruption of this interaction by imatinib seems likely to explain its Aβ-lowering activity.

Figure 6:
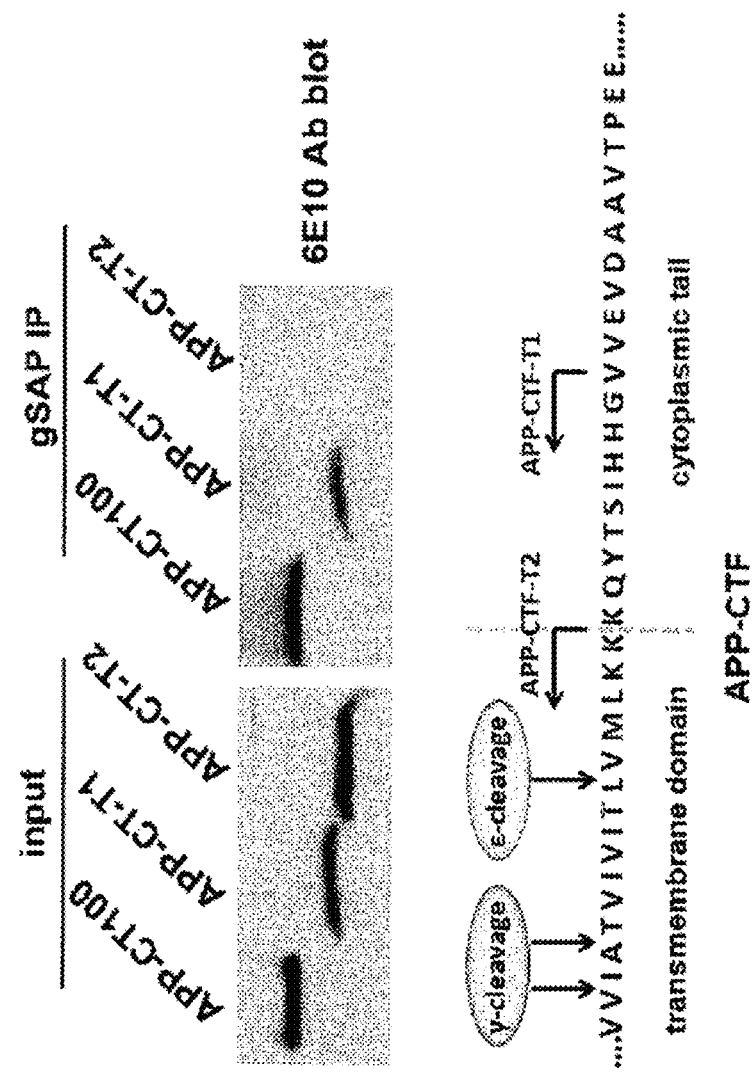
FIG. 6 shows truncation of APP-CTF and immunoprecipitation using gSAP antibody through gSAP, demonstrating that gSAP interacts with the juxtamembrane region of APP-CTF. APP-CTF-T1 is the truncated form of APP-β-CTF spanning from its N-terminus to HHGV$^{64}$. APP-CTF-T2 is the truncated form of APP-β-CTF spanning from its N-terminus to VMLKK$^{55}$. Truncated forms are overexpressed in HEK293 cells and immunoprecipitated with gSAP antibody. 6E10 antibody is used for immuno-detection.

The site of interaction between gSAP and APP is determined to be in the juxtamembrane region of APP-CTF (FIG. 6). APP-CTF is cleaved by γ-secretase in the middle of its transmembrane domain to generate Aβ (γ-cleavage) and near its cytosolic membrane boundary to generate APP intracellular domain (AICD) (ε-cleavage). The effect of gSAP on AICD production is examined in N2a cells overexpressing APP695. Both gSAP knockdown and imatinib treatment increases levels of AICD (supplementary FIG. 7a). gSAP overexpression in HEK293 cells reduces AICD production (supplementary FIG. 7b). These results indicate that gSAP differentially regulates γ- and ε-cleavage of APP-CTF to form Aβ and AICD respectively.

To determine whether our findings are relevant to AD pathology, the effects of gSAP on soluble Aβ levels and on plaque development are examined in vivo. A gSAP knockdown mouse line is generated by integration of tetracycline-inducible gSAP shRNA vector into the mouse genomic locus. Upon induction, gSAP mRNA level in the mice brain is reduced by ~85%. To evaluate the effect of gSAP on Aβ levels in vivo, gSAP RNAi mice are cross-bred with an AD mouse model with APPswe and PS1Δ9 mutations (AD 2×mice) (Jankowsky et al. 2001). After 1 month gSAP shRNA induction, Aβ40 and Aβ42 levels in the cross-bred mice are lowered by ~28% and ~32%, respectively. To evaluate the effect of gSAP on plaque development in AD 2×mice, recombinant adeno-associated virus 2 (AAV2) carrying gSAP shRNA is injected into plaque-developing hippocampus on one side of the brain, while the contralateral side receives the AAV2 without snRNA. Amyloid plaque development on the ipsilateral side of gSAP knockdown is suppressed by 26±8% (p<0.001, n=4) as compared to the contralateral side after 1 month. These data indicate that gSAP plays a critical role in Aβ formation and plaque development in vivo.

To summarize, gamma-secretase processes diverse substrates with low homology at their cleavage sites. The various roles of γ-secretase during development and in tissue homeostasis require that its activity be tightly regulated. Recent reports have shown the existence of biological molecules that modify the selectivity of cleavage by γ-secretase. The discovery of gSAP, a novel protein the function of which is previously unknown, and its ability to selectively stimulate Aβ formation, enables new strategies for the development of drugs to address AD and other Aβ-mediated diseases, such as Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloidosis, Parkinson's disease, Huntington's disease, prion disease and/or vascular, neurological, and/or neurodegenerative disorders related to the abnormal expression or accumulation of tau or amyloid proteins such as Aβ. Inhibitors of gSAP will selectively prevent β amyloid formation without affecting other key functions of γ-secretase. In support of this view, we demonstrate that a widely used anti-cancer drug, imatinib, achieves its Aβ-lowering effect by preventing gSAP activation of γ-secretase to generate Aβ, but without affecting other γ-secretase functions. The discovery of potent and direct pharmacological inhibitors of gSAP should facilitate the development of novel therapeutic reagents for the treatment of Alzheimer's disease.

gSAP is found to exist in a variety of animal species, e.g., as depicted in FIG. 1, and is highly conserved. A gSAP peptide is a peptide which is
  a. at least 60%, preferably at least 70%, e.g., at least 80%, for example at least 90% similar to a sequence selected from the sequences depicted in FIG. 1, using a BLAST algorithm (see e.g. blast.ncbi.nlm.nih.gov/Blast.)
  b. a peptide having residues corresponding to the conserved residues in bold in FIG. 1, or
  c. a peptide comprising the sequence Seq ID No. 7 (LWDHPMSSNIISR) and/or Seq ID No. 8 (NHVTRLLQNYKK), or In one aspect the invention provides a gSAP peptide as defined above isolated and purified from its natural environment, for example a transgenic gSAP peptide, e.g. produced by a bacterial, baculovirus or mammalian cell.

In another aspect, the invention provides a vector comprising a gene for a gSAP peptide operably linked to a heterologous promoter.

In another aspect, the invention provides a cell containing a heterologous gene expressing a gSAP peptide.

In another aspect the invention provides inhibitory RNA constructs capable of inhibiting gSAP expression in a mammalian cell.

In another aspect, the invention provides
  a. monoclonal antibodies to gSAP, e.g., capable of inhibiting its interaction with gamma-secretase and so inhibiting or reducing as Aβ production and accumulation;
  b. vaccines comprising an immunogenic fragment of gSAP in combination with a suitable adjuvant and/or carrier; and
  c. immunogenic conjugates comprising an immunogenic fragment of gSAP linked to an immunogenic carrier.

In another aspect, the invention provides gSAP knockout mammals, e.g., mammals, for example mice, wherein their gene for gSAP is disrupted.

In another aspect, the invention provides the use of a gSAP peptide, e.g. as defined above, in an assay to identify compounds which inhibit AP-deposition, e.g., a method of identifying an inhibitor of AP-deposition, comprising one or more of the following:

a. measuring binding of test compounds to a gSAP peptide, e.g., as defined above,
  i. e.g., in a competitive binding assay,
  ii. e.g., using labeled derivatives of imatinib:

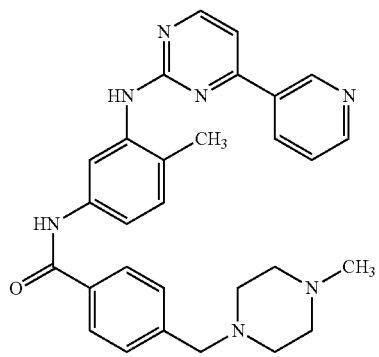 [SMILES: Cc1ccc(NC(=O)c2ccc(CN3CCN(C)CC3)cc2)cc1Nc1nccc(-c2cccnc2)n1]

iii. e.g., labeled by substitution by or modification with a labeling group at the methylpipirizinyl moiety,
  iv. e.g., selected from
    1. photolabeled derivatives, e.g., 4-azido-2-hydroxy-N-(4-methyl-3-(4-(pyridin-3-yl)pyrimidin-2-ylamino)phenyl)benzamide,
    2. radiolabeled derivatives, e.g., 4-azido-2-hydroxy-5-$^{125}$iodo-N-(4-methyl-3-(4-(pyridin-3-yl)pyrimidin-2-ylamino)phenyl)benzamide, or $^3$H-imatinib, and
    3. biotinylated derivatives, e.g., selected from IC339239 and IC2000001 (an inactive control compound):

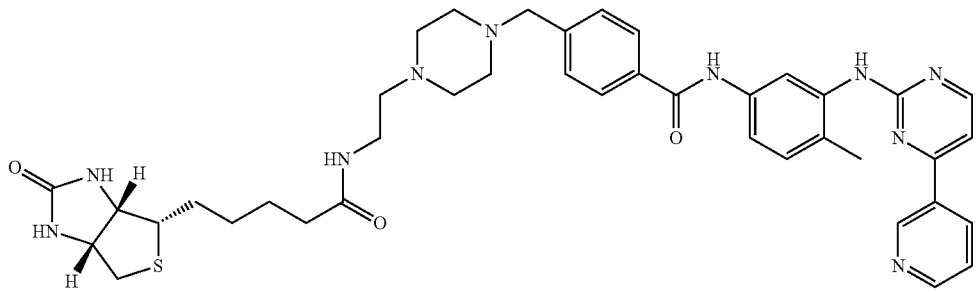

IC339239: active

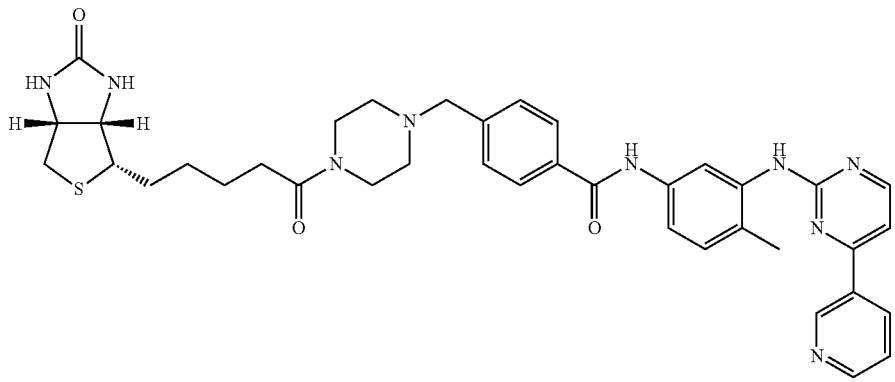

IC200001: inactive

The invention thus additionally provides labelled derivatives of imatinib, e.g., as described above.

The invention additionally provides a method of identifying persons at risk of developing AD comprising checking for elevated expression levels and/or mutations in gSAP relative to normal values as identified using a control population.

According to a further feature of this aspect of the invention there is provided a method for producing an inhibitory effect against the accumulation of abnormal protein aggregates in a warm-blooded animal, such as man, in need of such treatment which comprises administering to said animal an effective amount of a compound of formula (I), or a pharmaceutically acceptable salt thereof.

Furthermore, the compounds of this invention are useful in the treatment, control and management of diseases characterized by accumulation of abnormal protein aggregates, especially in the brain—for example, diseases such as Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloidosis, Parkinson's disease, Huntington's disease, prion disease and/or vascular, neurological, and/or neurodegenerative disorders related to the abnormal expression or accumulation of tau or amyloid proteins such as Aβ. Such abnormal protein aggregates include, for example, i) amyloid plaques and neurofibrillary tangles, and ii) precipitates of tau or amyloid proteins such as Aβ.

Accordingly, the present invention provides methods of treatment of Alzheimer's disease, progressive supranuclear palsy, Down Syndrome, memory and cognitive disorders, dementia, amyloid neuropathies, brain inflammation, nerve and brain trauma, vascular amyloidosis, cerebral hemorrhage with amyloeiosis, Parkinson's disease, Huntington's disease, prion disease and/or vascular, neurological, and/or neurodegenerative disorders related to the abnormal expression or accumulation of tau or amyloid proteins such as Aβ, comprising administering an effective amount of a compound to inhibit gSAP activity.

Compounds useful to inhibit gSAP activity include known small molecules, e.g.
  a. Imatinib and other compounds as disclosed in International Patent Publication No. WO 03/057165 and in U.S. Pat. No. 5,521,184, the contents of which are incorporated herein by reference;
  b. Compounds as described in WO 05/072826; J. Zimmermann et al., Bioorganic & Medicinal Chem. Lett., 7(2): 187-192; EP 1 533 304; WO 04/005281; WO 05/039586; U.S. Pat. No. 5,521,184; and WO 04/110452, the contents of which are incorporated herein by reference; and
  c. Compounds as disclosed in WO/2008/153974, WO/2008/153959, and WO/2008/057599, the contents of which are incorporated herein by reference.

Compounds useful to inhibit gSAP activity also include novel biotherapeutics, as described herein, including
  a. Inhibitory RNA molecules, e.g., selected from double-stranded, hairpin, sense or antisense RNA corresponding to a portion of the mRNA for gSAP, and capable of inhibiting gSAP transcription or translation; for example,
    i. siRNAs comprising sense sequence e.g, AUGCAGAGCUGGACGACAUUU and antisense sequence e.g. 5'-P.AUGUCGUCCAGCUCUGCAUUU; or
    ii. hairpin transcripts produced by a gSAP shRNA coding sequence, e.g.

TCCCGGAACTCCATGATTGACAAATTTCAAGAGAATTTGTCA

ATCATGGAGTTCC TTTTTA or

TGCTGTTGACAGTGAGCGCGGAAATAGAGTGGTGATTAAAT

AGTGAAGCCACAGATGTATTTAATCACCACTCTATTTCCATG

CCTACTGCCTCGGA;

b. Vectors and cells producing inhibitory RNA molecules, e.g. recombinant adeno-associated virus 2 (AAV2) carrying gSAP shRNA;
  c. Antibodies to gSAP, especially monoclonal antibodies, for example antibodies raised against fragments from the C-terminal region, e.g., 16K-gSAP, for example antibodies raised against the peptide CFEGHDNVDAEFVEEAALKHT (corresponding to aa 829-848 of human gSAP with an N-terminal cysteine attached for conjugation) as described more fully below;
  d. Vaccines for gSAP, comprising a fragment of gSAP in combination with an immunogenic adjuvant and/or carrier, e.g., conjugated to an immunogenic carrier, e.g., a bacterial toxoid, e.g. diphtheria or tetanus toxoid, keyhole limpet hemocyanin (KLH), blue carrier protein, ovalbumin, or bovine serum albumin, and/or delivered together with an adjuvant, e.g. Freund's adjuvant or alum adjuvant.

The invention provides, in a further embodiment, methods to identify candidates for treatment with gSAP-targeted therapy, e.g., e.g. administration with gSAP inhibitors or vaccines as described above, the methods selected from, e.g., 1. Measuring gSAP expression, e.g., using antibodies to gSAP or quantitative PCR for gSAP expression, wherein elevated expression is seen in candidates for treatment with gSAP targeted therapy; or 2. Identifying patients having mutations affecting gSAP or gSAP expression, e.g., having haplotypes comprising any of the following groups of SNPs
  a) rs6976567|rs1468682|rs1819814,
  b) rs1468682|rs1819814|rs4729535,
  c) rs1819814|rs4729535|rs4729540,
  d) rs7781642|rs6955503|rs7776973
wherein patients having such mutations or haplotypes are candidates for treatment with gSAP targeted therapy;

3. Identifying patients having mutations affecting gSAP activity, e.g., mutations at the sequence encoding the juxtamembrane region of APP-CTF, wherein patients having such mutations or haplotypes are candidates for treatment with gSAP targeted therapy.

The invention further provides diagnostic assay kits for use in such methods, e.g., comprising monoclonal antibodies to gSAP, or primers to the gSAP gene or fragments thereof, and oligonucleotide probes to detect mutations in the gSAP gene or in the juxtamembrane region of the gene for APP-CTF.

Example 1

Synthesis of Labeled Imatinib Derivatives 2,5-dioxopyrrolidin-1-yl 4-azido-2-hydroxybenzoate (NHS-ASA) is purchased from ProChem. Inc (Rockford, Ill.). 6-Methyl-$N^1$-(4-(pyridin-3-yl)pyrimidin-2-yl)benzene-1,3-diamine and N-(4-methyl-3-(4-(pyridin-3-yl)pyrimidin-2-ylamino)phenyl)-4-(piperazin-1-ylmethyl)benzamide (N-desmethyl imatinib) are purchased from ChemPacific Inc (Baltimore, Md.). 2,5-dioxopyrrolidin-1-yl 5-((3aS,4S,6aR)-2-oxo-hexahydro-1H-thieno[3,4-d]imidazol-4-yl)pentanoate (Biotin-OSu), N-(chloro(dimethylamino)methylene)-N-methylmethanaminium hexafluorophosphate (TCFH), trifluoroacetic acid (TFA), 1H-benzo[d][1,2,3]triazol-1-ol (HOBt) and N,N-diisopropylethyl amine (DIPEA) are purchased from Sigma-Aldrich (St. Louis, Mo.). Tert-butyl 2-(piperazin-1-yl)ethylcarbamate is purchased from Astatech Inc (Bristol, Pa.).

(a) Synthesis and Kinase Profiling of Biotin-Imatinib (Active and Inactive Form):

Two forms of biotin imatinib are synthesized, one having the characteristic kinase activity of imatinib, and the other lacking kinase activity.

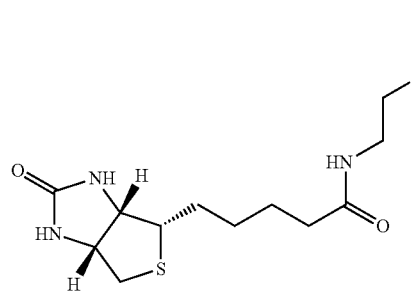
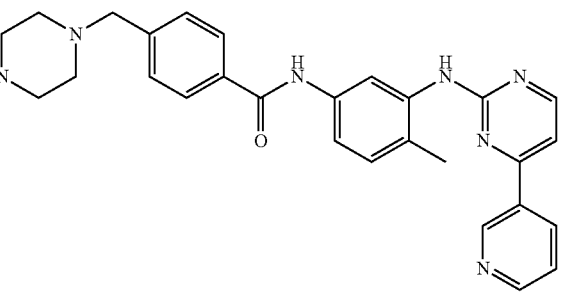
IC339239: active
IC200001: inactive
Inactive biotin-imatinib, (IC200001) is synthesized by reacting N-desmethyl imatinib with Biotin-OSu. Active biotin-imatinib, (IC339239) is synthesized from the key intermediates, tert-butyl 2-(piperazin-1-yl)ethylcarbamate and 6-methyl-$N^1$-(4-(pyridin-3-yl)pyrimidin-2-yl)benzene-1,3-diamine, via 4 steps:
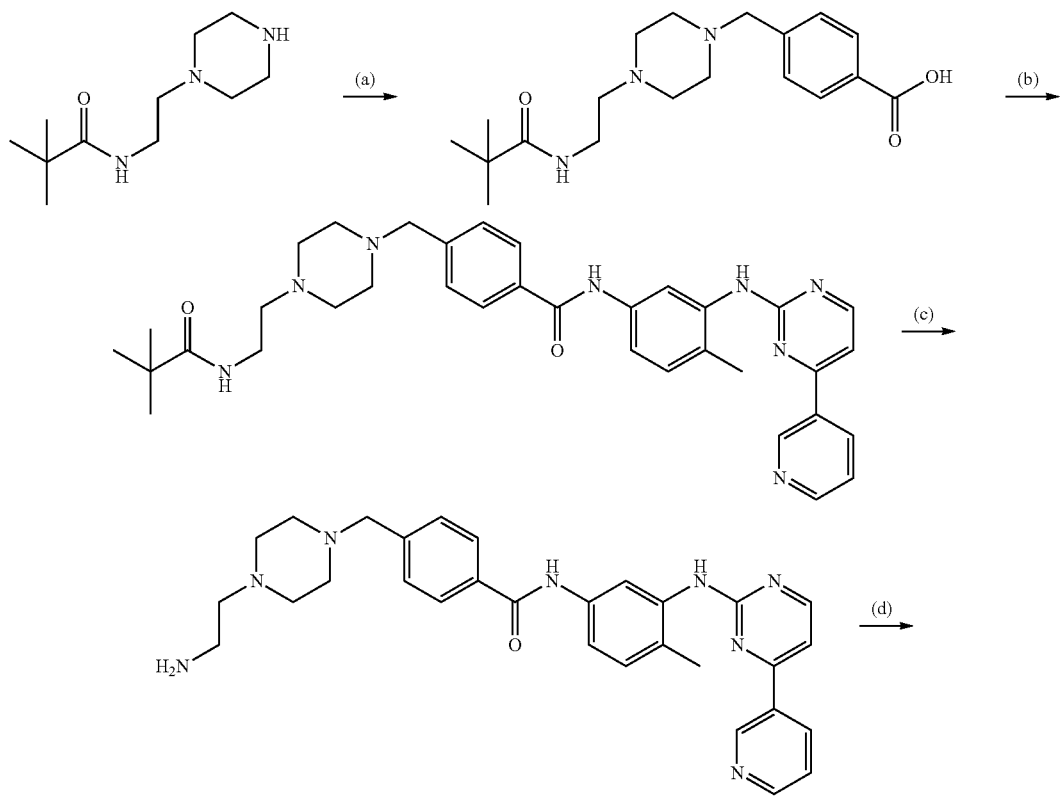

-continued

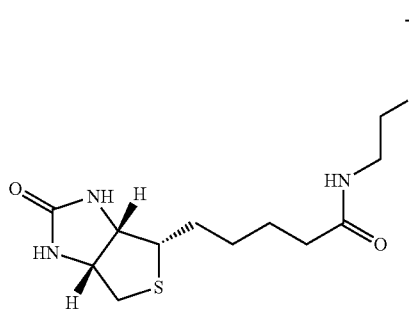 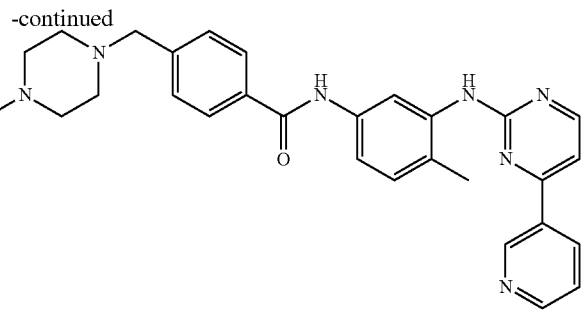

IC339239

Reagents and Conditions: (a) 4-(bromomethyl) benzoic acid, K$_2$CO$_3$, DMF, r.t., 2 h. (b) 6-methyl-N$^1$-(4-(pyridin-3-yl)pyrimidin-2-yl)benzene-1,3-diamine, TCFH, DIPEA, DMF, r.t., overnight. (c) TFA, CH$_2$Cl$_2$, r.t., 30 min. (d) Biotin-OSu, HOBt, DIPEA, r.t., overnight, and then HPLC purification.

The kinase profiling is performed by Millipore Inc. using the standard assays for Abl kinase and PDGF receptor (ATP=45 μM). Compound IC200001 shows no significant inhibitory activity toward either kinase, while compound IC339239 has an IC50 of 146 nM against Abl kinase (imatinib has an IC50 of 79 nM) and an IC50 of 6.6 μM against PDGF receptor (imatinib has an IC50 of 4.8 μM). Thus, we refer to IC200001 as "inactive biotin-imatinib" and IC339239 as "active biotin-imatinib".

(b) Synthesis of an Imatinib Derived Photo-Affinity Label, G01:

An imatinib derivative, 4-azido-2-hydroxy-N-(4-methyl-3-(4-(pyridin-3-yl)pyrimidin-2-ylamino)phenyl)benzamide, is capable of being photoactivated. N,N-Diisopropylethylamine (DIPEA) (63 μl, 0.36 mmol) is added to a solution of NHS-ASA (50 mg, 0.18 mmol), HOBt (25 mg, 0.18 mmol), and 6-Methyl-N$^1$-(4-(pyridin-3-yl)pyrimidin-2-yl)benzene-1,3-diamine (50 mg, 0.18 mmol) in DMF (2 ml). The reaction mixture is stirred at room temperature overnight under argon atmosphere. The generated crude product is purified by a semi-preparative HPLC to give 54 mg of the titled compound with a yield of 68%. The product, G01, 4-azido-2-hydroxy-N-(4-methyl-3-(4-(pyridin-3-yl)pyrimidin-2-ylamino)phenyl)benzamide, is confirmed by mass spectral analysis using an ESI-MS in the positive mode [M+H]$^+$, demonstrating a m/z of 439.1.

(c) Radioiodination of G01 by $^{125}$I is performed without carrier using a modification of a Chloramine-T procedure and the iodinated product is purified by HPLC. Specifically, in a UV protected "V" vial, total volume 0.9 ml, ~10 mCi of $^{125}$I stock isotope (volume=25 μl) is added to 200 μl of 0.2M phosphate buffer, pH 7.2. G01 is dissolved to 1 mg/ml in ethanol and 25 μl of this solution is combined with chloramine-T at 1 mg/mL in water (50 μl) and then added to the V-vial. The reaction proceeded for 1 min and is terminated by the addition of 50 μL of 1 mg/ml meta-bisulfite. The reaction mixture is chromatographed on a 25 cm Waters RP-C18 column, using 0.1% TFA in water as the "A" solvent and 0.1% TFA in acetonitrile as the "B" solvent. A gradient is run at 1 ml/min from 0% B to 50% B for 45 minutes and held at 50% B for 15 minutes. The product demonstrated a retention time of 54.5 min as followed by radiochemical detection, and had a specific activity of 2000 Curies per millimole. The I$^{125}$ labeling experiment is performed by PerkinElmer Life and Analytical Sciences, Inc. The structures of G01, $^{125}$I-G01, as compared to imatinib are:

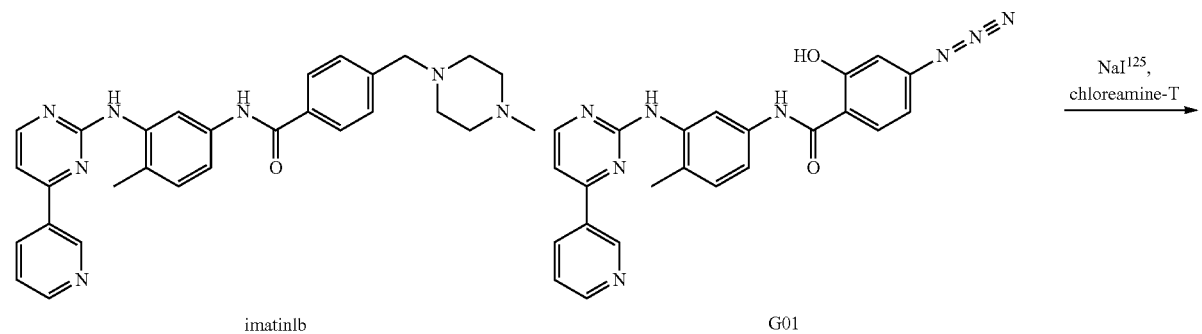

imatinib                    G01

-continued

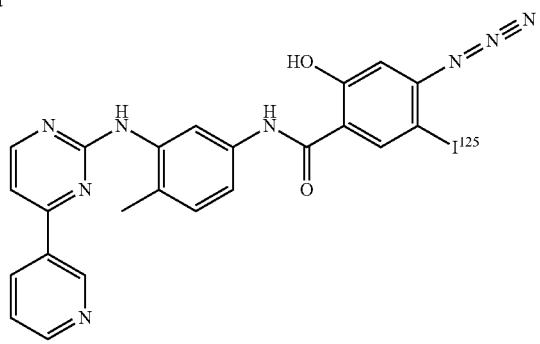

125I-G01

$^3$H-G01 is prepared by ViTrax Radiochemicals via catalytic tritium exchange of G01. The labeled product is purified by HPLC. The composition of the purified product is verified by co-injection of the tritium labeled product with its cold precursor and both compounds co-chromatographed on an analytical HPLC.

(d) Cellular Aβ Production Assays and Incubation with G01.

Neuroblastoma 2a cells stably overexpressing human APP695 are treated with 10 μM G01 for 3 hr. Cells treated with DMSO, or DMSO plus imatinib are used as controls. After 3 hr, conditioned medium is collected and Aβ immunoprecipitation is conducted using 4G8 antibody. The immunoprecipitated Aβ is separated on 10-20% Tris-tricine gel, transferred to PVDF membrane and detected by 6E10 antibody. Although not as potent as imatinib, G01 significantly reduces Aβ compared to the DMSO vehicle at levels of 10 μM.

Example 2

Immobilization of Imatinib and Affinity Purification

For affinity purification, HEK293 cells are homogenized with 10 mM Hepes, 250 mM sucrose, pH 7.4 in the presence of protease inhibitors. After cell debris is cleared by centrifugation at 1,000 g for 5 mins, the supernatant is subjected to ultracentrifugation at 100,000 g for 1 h. The membrane pellet is then solubilized on ice in 50 mM Hepes, 150 mM NaCl, 5 mM MgCl$_2$, 5 mM CaCl$_2$, and 1% CHAPSO containing protease inhibitors (Roche Inc. cat#04 693 132 001) for 1 h and subject to ultracentrifugation for 1 h at 100,000 g. The soluble membrane extracts are incubated with Myonen™ streptavidin T1 beads (cat#656-01, Invitrogen) containing bound active biotin-imatinib for 3 hr at 4° C. Subsequently, the beads are washed three times with lysate buffer. Bound proteins are eluted with tricine SDS-PAGE sample buffer and separated on 10-20% tris-tricine gels. For immunoblotting, the gel is then transferred to PVDF membrane and probed with γ-secretase antibodies: PS1 antibody (cat#529592) and Pen-2 antibody (cat#NE1008) are from EMD Biosciences and nicastrin antibody is from BD Transduction Laboratories (cat#612290). Silver staining is used to identify protein bands in SDS-PAGE gels. The ~16 kDa band is excised, trypsinized, and sequenced by tandem MS/MS mass spectrometry.

To identify the target responsible for imatinib's selective Aβ-lowering activity, we synthesize a biotinylated derivative of imatinib, "biotin-imatinib, which specifically captures solubilized γ-secretase components, including presenilin-1, PEN2, and nicastrin. To identify the protein with which imatinib directly interacts, we synthesized a photoactivatable azido imatinib derivative, G01. When $^{125}$I-G01 is incubated with a membrane preparation followed by photolysis, none of the four components of γ-secretase are labeled. Rather, $^{125}$I-G01 labels a ~16 kDa protein, which co-immunoprecipitates with the more slowly migrating 18 kDa presenilin-1-CTF. This result is confirmed by intact cell photolabeling using cell permeable $^3$H-G01. Similar to $^{125}$I-G01, the $^3$H-imatinib derivative does not bind to any of the four γ-secretase components, but does label a band of ~16 kDa that co-immunoprecipitated with PS1.

To purify the potential target protein, immobilized active biotin-imatinib is incubated with solubilized membrane preparations and bound proteins are separated by SDS-PAGE. After silver staining, a ~16 kDa band is observed. Peptide fragments, derived from this band after trypsin digestion, and analyzed by tandem mass spectrometry, corresponded to the C-terminal region of an uncharacterized protein, pigeon homologue protein (PION) (human accession number: NP_059135). The identification is made based on two unique tryptic peptides ($^{766}$LWDHPMSSNIISR$^{778}$ and $^{779}$NHVTRLLQNYKK$^{790}$) covering approximately 20% of the 16 KDa fragment. Its sequence, especially the C-terminal region, is highly conserved among multiple species from chicken to human. Expression pattern analysis indicates that this gene is expressed in diverse tissues. We characterize PION as a gamma-secretase activating protein (gSAP).

Example 3

In Vitro and Intact Cell Photolabeling

For in vitro labeling, membrane pellets are prepared as described above and resuspended in 50 mM Hepes, pH 7.4, 150 mM NaCl, 5 mM MgCl$_2$, 5 mM CaCl$_2$. Resuspended membranes are incubated with 20 nM $^{125}$I-G01 for 3 hr at 4° C. prior to photolysis using a compact UV lamp (4 watt, model UVGL-25, UVP Inc.) at 254 nM for 2 mins. To examine labeling specificity, 50 μM imatinib is added to a parallel assay. After photolysis, membranes are pelleted by ultracentrifugation at 100,000 g for 1 h and solubilized with 50 mM Hepes, 150 mM NaCl, 1% CHAPSO, 5 mM MgCl$_2$, 5 mM CaCl$_2$. The supernatant is pre-cleared with protein G plus/protein A beads (EMD Biosciences, cat#IP05) for 30 min and proteins are precipitated using PS1 antibody (EMD Biosciences, cat#529592) coupled to protein G plus/protein A beads for 2 h before washing with lysate buffer 4 times. The bound material is eluted in SDS-tricine sample buffer and separated using 10-20% Tris-tricine gels, followed by transfer to PVDF membrane. The membrane is dried and exposed to Kodak MS film for autoradiography. For intact cell labeling, human embryonic kidney cells (HEK293) grown to ~80% confluency (~$10^7$ cells) are incubated with 0.1 µM $^3$H-G01 in Opti-MEM for 2 hours in an incubator at 37° C., with 5% $CO_2$ before being transferred to ice for an additional hour. Medium is removed and cells are washed twice with cold phosphate buffered saline (PBS), pH 7.4. Photolysis is conducted on ice for 2 min using a compact UV lamp (4 watt, model UVGL-25, UVP Inc.) at 254 nM. As controls, cells are incubated either without UV crosslinking or in the presence of 50 µM unlabeled imatinib. After photolysis, cells (~$10^7$ cells for each treatment) are immediately homogenized in 1 ml 50 mM Hepes, pH 7.4, 150 mM NaCl, 1% CHAPSO, 5 mM $MgCl_2$, 5 mM $CaCl_2$ with protease inhibitor mixture (Roche) on ice. After pre-clearing with protein G plus/protein A beads, proteins are immunoprecipitated for 2 hr using 10 µl of the PS1-loop antibody (cat#529592 EMD Biosciences). The immunoprecipitate is washed 3 times with lysis buffer. The immuno-purified (IP) material is eluted with SDS sample buffer and product is separated using a 10-20% Tris-Tricine SDS-PAGE gel, transferred to PVDF membrane, and the membrane dried and exposed to Kodak MS film for autoradiography.

Example 4 gSAP Antibody Production and Metabolic Labeling

Rabbit polyclonal antiserum against gSAP is generated by injecting New Zealand White rabbits with the peptide CFEGHDNVDAEFVEEAALKHT (corresponding to aa 829-848 of human gSAP with an N-terminal cysteine attached for conjugation) coupled to keyhole limpet hemocyanin (cat#PI-77563, Fisher Scientific). Rabbit injections, bleeds, and housing are performed by Cocalico Biologicals (Reamstown, Pa.). The antibody is purified by passing serum through a Sulfolink resin (Thermo Scientific, cat#44999) with the antigenic peptide immobilized and eluted following the company instructions. For pulse-chase labeling, neuroblastoma 2a cells are incubated for 30 min with DME minimal essential medium deficient in methionine and cysteine (Met-Cys-DMEM). Cell proteins are labeled with Met-Cys-DMEM containing EXPRESS $^{35}$S Protein Labeling Mix (cat#NEG772014MC, Perkin Elmer) for 15 min at 37° C. The chase periods are initiated by replacing the medium with full culture medium 50% DMEM/50% Opti-MEM, 5% fetal bovine serum (FBS) and cells are incubated at 37° C. for various times. For continuous labeling, cells are labeled with $^{35}$S Protein Labeling Mix (Perkin Elmer) for 4 hrs without chase, and washed with Dulbecco's Phosphate Buffered Saline (DPBS). Cell monolayers are lysed in RIPA buffer (10 mM Tris, 1% deoxycholate, 1% Triton X-100, 0.1% SDS, at pH 7.4) containing protease inhibitors. The lysates are clarified by centrifugation for 20 min at 13,000 rpm and the supernatant is pre-cleared with protein G plus/protein A beads followed by immunoprecipitation using gSAP antibody for 2 hrs. The beads are incubated with Tris-tricine sample buffer to elute bound proteins which are then separated by 10-20% Tris-tricine gel, transferred to PVDF membrane, and exposed to Kodak MR film for autoradiography.

Example 5

Cellular Knockdown and Overexpression

For cellular gSAP knockdown experiments, small interfering RNA (siRNA) of gSAP is purchased from Dharmacon Inc. The sequences of the siRNA used are as follow: sense sequence: AUGCAGAGCUGGACGACAUUU; antisense sequence: 5'-P.AUGUCGUCCAGCUCUGCAUUU. Neuroblastoma 2a cell line stably overexpressing APP695 is transfected with siRNA using DharmaFect 2 reagent at a concentration of 50 nM following instructions provided by the manufacturer. Non-targeting control siRNA (cat#D-001810-01, Dharmacon Inc.) is transfected in parallel as control. Short hairpin RNA (shRNA) of gSAP is purchased from Open Biosystems and transfected into cells using lipofectamine 2000. The sequence of mouse gSAP shRNA in pGIPZ shRNAmir-GFP vector is follows: TGCTGTT-GACAGTGAGCGCGGGTATAGCCTTATTTGCATAT-AGTGAAGCCACAGA TGTATATGCAAATAAGGC-TATACCCATGCCTACTGCCTCGGA. The sequence of human gSAP shRNA in pGIPZ shRNAmir-GFP vector is as follows: TGCTGTTGACAGTGAGCGCGGAAATA-GAGTGGTGATTAAATAGTGAAGCCACAG ATGTATT-TAATCACCACTCTATTTCCATGCCTACTGCCTCGGA. The knockdown efficiencies are examined using a real time RT-PCR kit (cat#12183, Invitrogen).

For gSAP overexpression in cells, mammalian expression vector pReceiver-M07 with the full length and the 16 KDa C-terminal fragment (amino acid sequence 733-854) of gSAP coding a C-terminal HA tag is purchased from Genecopoeia Inc. The plasmid is transformed into XL1 blue competent cells (cat#200249-11, Stratagene) and purified using an EndoFree Maxi preparation kit (cat#12362, Qiagen). Plasmid is transfected into a stable HEK293 cell line overexpressing APP695, containing the Swedish mutation, using Fugene 6 (cat#11815091001, Roche).

To assay Aβ, the medium is removed after 48 h of transfection and replaced with Opti-MEM for 3 h incubation. Aβ is then immunoprecipitated from conditioned medium using the 4G8 antibody. Quantitation of Aβ levels in the conditioned medium is also assessed using Aβ40 and Aβ42 ELISA kits (Invitrogen). The procedures are carried out according to the manufacturer's instructions.

When siRNA is used to reduce gSAP level (by 72±15%) in neuroblastoma cells overexpressing APP695, the level of Aβ decreases about 50%. The addition of imatinib has little or no additional effect on Aβ levels. shRNA-mediated gSAP knockdown (by 65±12%) in HEK293 cells expressing APP Swedish mutation also results in a decrease of Aβ40 and Aβ42 levels of 61% and 48%, respectively. Conversely, overexpression of gSAP in HEK293 cells expressing the APP Swedish mutation stimulates Aβ production by approximately 38%; the increase is abolished by imatinib treatment.

Example 6

Co-Immunoprecipitation

For co-immunoprecipitation, ~$10^7$ cells are lysed with 1 ml of 50 mM Hepes, 150 mM NaCl, 1% CHAPSO, 5 mM $MgCl_2$, 5 mM $CaCl_2$, with protease inhibitors for 30 min on ice. Cell debris and nuclei are removed by centrifugation at 13,000 rpm for 20 min. After pre-clearing with protein G plus/protein A beads for 30 min, immunoprecipitation is performed using the corresponding antibody and 30 μl beads for 2 hr on ice. The beads are washed 4 times with the lysate buffer and eluted with 30 μl of SDS sample buffer at 95 degree for 5 mins. Immunoprecipitated proteins are resolved by SDS-PAGE and analyzed by immunoblot. Presenilin 1 loop antibody AB14 (EMD Biosciences #529594) is used to detect PS1-NTF, Pen-2 antibody is purchased from EMD Biosciences (#NE1008). Nicastrin antibody is from BD Biosciences (#612290). HA monoclonal antibody (#A0089) and Myc tag polyclonal antibody (#A00172) are from Genscript Inc. APP-CTF is detected using the 369 antibody (Xu et al. 1998). 6E10 (#SIG39320) and 4G8 (#S1039220) antibodies from Covance are used to detect Aβ.

Solubilized γ-secretase components from HEK293 cell membrane preparations are bound to the immobilized imatinib derivative, biotin-imatinib, and detected by immunoblotting. Both biotin-coated beads and an inactive biotin-imatinib derivative served as controls. Endogenous γ-secretase components are detected by specific antibodies to Nicastrin, PS1-CTF and Pen-2. Photoactivatible $^{125}$I and $^{3}$H-G01 are used to label membrane preparations or intact HEK293 cells, respectively. After lysis and immunoprecipitation with PS1 antibody, bound proteins are separated by 10-20% Tris-tricine SDS-PAGE. A 16 kDa band is detected by autoradiography in both photolabeling conditions. This labeling is eliminated by co-incubation with 50 μM unlabeled imatinib before photolysis. The same membranes probed with PS1-CTF antibody show that PS1-CTF migrates with a slower mobility than the 16 kDa band and is not labeled by G01. Proteins in HEK293 cell lysates that bind biotin-imatinib beads are separated on SDS-PAGE and visualized with silver staining. A ~16 kDa band is detected (arrow and label "gSAP") that does not bind to biotin alone or to inactive biotin-imatinib. After trypsinization, the 16 kDa band is identified as the C-terminal domain of gSAP by MS/MS mass spectrometry.

$^{35}$S-methionine pulse-chase labeling of endogenous gSAP in N2a cells is followed by immunoprecipitation using a polyclonal antibody raised against the C-terminus of gSAP. gSAP is synthesized as the full length 98 kDa-precursor protein and rapidly processed into a C-terminal fragment migrating at 16 kDa. After 4 hrs of continuous $^{35}$S-methionine labeling (steady-state conditions), the predominant cellular form of gSAP is the 16 kDa species. Intact N2a cell labeling is performed by incubation with $^{3}$H-G01. Cells are lysed with RIPA buffer and proteins were immunoprecipitated with gSAP antibody. After separation on SDS-PAGE and radiography, gSAP-16K is found to be specifically labeled by $^{3}$H-G01; this labeling is quenched by pre-incubation of cells with 50 μM imatinib. gSAP overexpressed with or without PS1 in presenilin null embryonic stem cells bound biotin-imatinib is detected by immunoblotting. Under gSAP siRNA knockdown conditions, PS1 no longer captures biotin-imatinib.

Example 7

Gel Filtration Chromatography

N2a cells are labeled with $^{35}$S Protein Labeling Mix (Perkin Elmer) for 4 hrs as described above. Solubilized membrane preparations (0.2 ml, ~1 mg of solubilized protein, in 50 mM Hepes, 150 mM NaCl, 1% CHAPSO, 5 mM $MgCl_2$, 5 mM $CaCl_2$) are centrifuged for 1 h at 100,000 g to remove potentially aggregated material. The resulting supernatant is loaded onto a Superdex 200 10/300 GL column (Amersham Biosciences) of an AKTA fast performance liquid chromatography system (Amersham Biosciences). Fractionation is performed in the lysate buffer at a flow rate of 0.5 ml/min and 1-ml fractions are collected for analysis. Each fraction is analyzed by western blot against γ-secretase antibodies. To detect endogenous gSAP, each fraction is immunoprecipitated with gSAP antibody. The immunoprecipitated materials are eluted with Tris-tricine sample buffer, separated by 10-20% Tris-tricine gel, transferred to PVDF membrane, and exposed to Kodak MR film for autoradiography.

Example 8

In Vitro γ-Secretase Assay

Membrane pellets are prepared from HEK293 cells transfected with APP-β-CTF (CT-100) as described above, and the membranes are washed with assay buffer (10 mM Hepes, 140 mM KOAc, 2.5 mM MgOAc, 0.1 mM $CaCl_2$, 1 mM ATP, pH 7.2) and pelleted at 100,000 g for 30 min at 4° C. Recombinant gSAP-16K (aa733-854 of the human gSAP) is expressed and purified from BL21 DE3 *E. coli*. The membranes are resuspended in 200 μl of assay buffer with 2 μg recombinant gSAP-16K or the same amount of BSA as control. A parallel system with 1 μM L685,458 (γ-secretase inhibitor) is also used as a control. The membrane suspension is pre-incubated at 4° C. for 1 hr and then incubated for 2 hr at 37° C. to allow in vitro generation of Aβ. The membranes are solubilized in ¼ volume of 200 mM Tris, pH 7.8, 760 mM NaCl, 24 mM EDTA, 10% Triton X-100, and insoluble material is removed by centrifugation at 10,000 g for 20 min. Aβ is immunoprecipitated from the lysate using 4G8 antibody, separated on 10-20% Tris-tricine gel, transferred to PVDF membrane, and subjected to autoradiography using Kodak MR film.

Example 9

Notch Cleavage Analysis

Plasmid coding NotchΔE (truncated Notch-1, lacking most of the Notch extracellular domain, with a C-terminal myc tag) is described previously (Netzer et al. 2003). Cells transfected with NotchΔE are co-transfected with gSAP-shRNA or gSAP plasmids. After two days of transfection, Notch expression and cleavage are detected with anti-myc antibody. The cleaved Notch intracellular domain (NICD) is detected with a cleavage-specific antibody (Notch1 Val-1744, Cell Signaling Inc.). Cells treated with L-685,458 serve as controls.

gSAP regulates Aβ production but does not influence Notch cleavage. siRNA-mediated knockdown of gSAP in N2a cells overexpressing APP695 results in lowered Aβ production. The Aβ-lowering effects of imatinib and of siRNA are not additive. Transfection with gSAP shRNA of HEK293 cells stably expressing human APP containing the Swedish mutation reduces the levels of both Aβ40 and Aβ42. gSAP overexpression in HEK293 cells increases Aβ levels and this effect is blocked by imatinib. Under either gSAP knockdown or overexpression conditions, Notch processing is not affected in HEK293 cells overexpressing extracellular domain truncated Notch (NotchΔE, with C-terminal myc tag). NICD is detected using a myc antibody and a cleavage-product specific antibody (Notch1 Val-1744). Recombinant gSAP-16K purified from *E. coli* stimulates Aβ production in an in vitro γ-secretase assay. The γ-secretase inhibitor, L685,458 (1 μM) abolishes Aβ production.

gSAP interacts with γ-secretase and APP-CTF, but not with NotchΔE. Membrane preparations from N2a cells are prepared, lysated with 1% CHAPSO, subjected to gel filtration, and detected by western blotting. Endogenous gSAP-16K co-migrates with γ-secretase components. Column void fraction=6. Immunoprecipitation of endogenous gSAP results in co-immunoprecipitation of γ-secretase components. In HEK293 cells that co-express NotchΔE-myc, APP-CTF, and gSAP-16K-HA, immunoprecipitation of gSAP-16K is associated with co-immunoprecipitation of APP-CTF but not of NotchΔE. Immunoprecipitation of APP-CTF, but not of NotchΔE, is associated with co-immunoprecipitation of gSAP-16K. Treatment with imatinib reduces the association between gSAP-16K and APP-CTF.

Example 10 gSAP RNAi Mice Line Generation and Aβ Level Measurement

RNAi mice are generated following the procedure as described before (Seibler et al. 2007). Specifically, exchange vector carrying gSAP shRNA coding sequence TCCCG-GAACTCCATGATTGACAAATTTCAAGAGAATTTGT-CAAT CATGGAGTTCCTTTTTA is under the control of a H1-Tet promoter. Using the recombinase-mediated cassette exchange (RMCE) technology, the vector is integrated into the mouse ES cell genome (B6/129S6 background). Subsequently, transfected ES cells are injected into tetraploid blastocyst to generated inducible RNAi mice. Heterozygous RNAi mice are then cross-bred with an AD mouse model with APPswe and PS1Δ9 mutations (AD 2×mice) to generate gSAP-RNAi AD mice. shRNA induction is conducted by introducing 2 mg/ml doxycycline (Sigma D-9891) in drinking water containing 10% sucrose. Control mice are fed with drinking water containing 10% sucrose. Drinking water is changed every second day and kept dark. gSAP knockdown efficiency in mice is assayed using quantitative real time RT-PCR. Total RNA is isolated following standard procedure and cDNA is synthesized using the Reverse Transcription Core Kit (Eurogentec). Real-time PCR reactions are performed using an iCycler Thermal cycler instrument (Bio-Rad). For mouse brain Aβ level measurements, 2 month old gSAP-RNAi AD mice are induced with doxycycline for 1 month and brain tissue is extracted with formic acid for ELISA assay.

Figure 3:
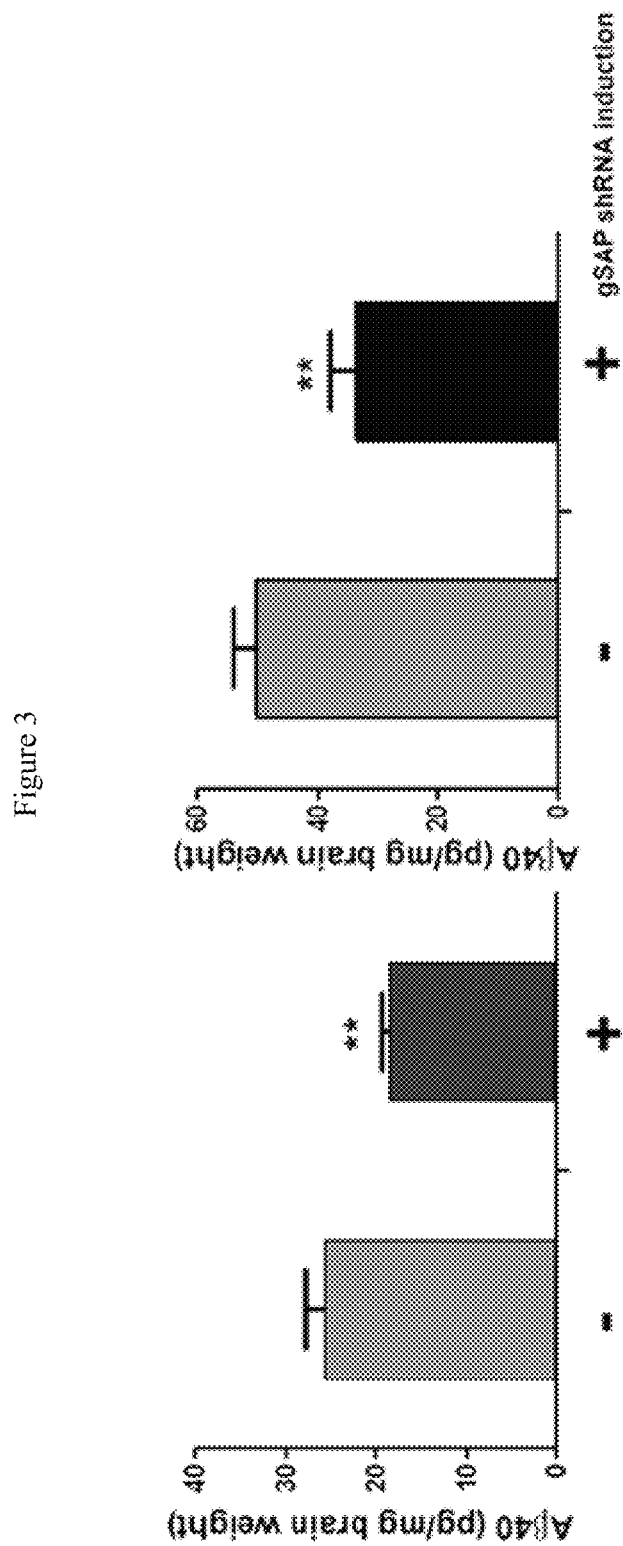
FIG. 3 shows inhibition of gSAP by shRNA reducing Aβ production and plaque development in an AD mice model.

Knockdown of gSAP reduces Aβ production and plaque development in AD mice models. gSAP RNAi-AD mice are generated by cross-breeding of double transgenic AD mice with inducible gSAP RNAi mice. gSAP shRNA expression (under doxycycline induction) reduces both Aβ40 and Aβ42 levels in the mice brain by ~28% and ~32%, respectively (**: P<0.01. n=4) (FIG. 3).

Example 11

Intra-Hippocampal Injections of AAV2-gSAP shRNA to PS/APP Transgenic Mice

Mouse GIPZ shRNAmir individual clone (V2LMM_88580: containing the hairpin sequence for mouse gSAP gene TGCTGTMACAGTGAGCGCGGG-TATAGCCTTATTTGCATATAGTGAAGCCACAGA TGTATATGCAAATAAGGCTATACCCATGCCTACTGC-CTCGGA) is purchased from Openbiosystems/Thermo Scientific. The hairpin region is excised and inserted into AAV2-siln4.1-MCS-EGFP vector (Vector biolabs) via BamHI and HindIII sites. The triple transgenic AD mice (6 months old) are analyzed for Aβ. The double transgenic AD mice (13 months old) are analyzed for plaques. For each group, mice are deeply anesthesized with a mixture of ketamine (100 mg/kg) and xylazine (10 mg/kg) and placed in a stereotaxic frame. AAV2 virus carrying AVV2-gSAP shRNA-GFP or AVV2-GFP is bilaterally injected into right or left hippocampus. Stereotaxic coordinates are determined according to Paxinos Atlas of the mouse brain: anteroposterior 2.18 mm, mediolateral 1.97 mm and dorso-ventral 2 mm. One µl of each AAV2 (shRNA for gSAP or GFP control) ($3.3 \times 10^{13}$ vg/ml) is injected for 5 min at a rate of 0.2 µl/min with a 10 ul Hamilton syringe equipped with a motorized injection pump. The injection needle is allowed to remain in the brain for an additional 5 min to prevent fluid extravasation. Mice are sacrificed 4 weeks after injection.

To determine Aβ levels, the hippocampus is removed and solubilized in 2% SDS containing protease inhibitors. The lysates are centrifuged at 13,000 rpm for 20 mins and the supernatant is used for ELISA analysis using Aβ40 and Aβ42 assay kits (Invitrogen Inc.).

For immunolocalization studies, mice are subjected to intracardiac perfusion with 0.1M PBS followed by 4% paraformaldehyde/PBS. After perfusion, brains are removed and post-fixed with 4% paraformaldehyde/PBS at 4° C. overnight, followed by incubation with 15% sucrose and then 30% sucrose for 24 hours. Cryo-protected brains are cut into 25-50 uM thick sections using a cryostat. Sections are labeled with the anti-Aβ antibody 6E10 (1:1000, Novus Biologicals) to visualize extracellular amyloid plaques and anti-EGFP antibody (1:500, Invitrogen) to visualize neurons positively transduced with the shRNA coding AAV virus using an M.O.M immunodetection kit (Vector laboratories, PK-2200). Imaging is performed using a Zeiss LSM510 confocal microscope.

Figure 4:
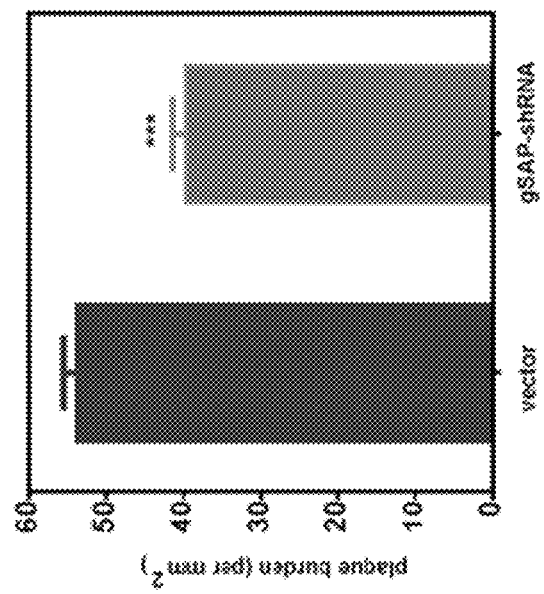
FIG. 4 shows effect of intrahippocampal injection of AAV2-carrying shRNA against gSAP in reducing amyloid plaque development in double transgenic AD mice.
Figure 5:
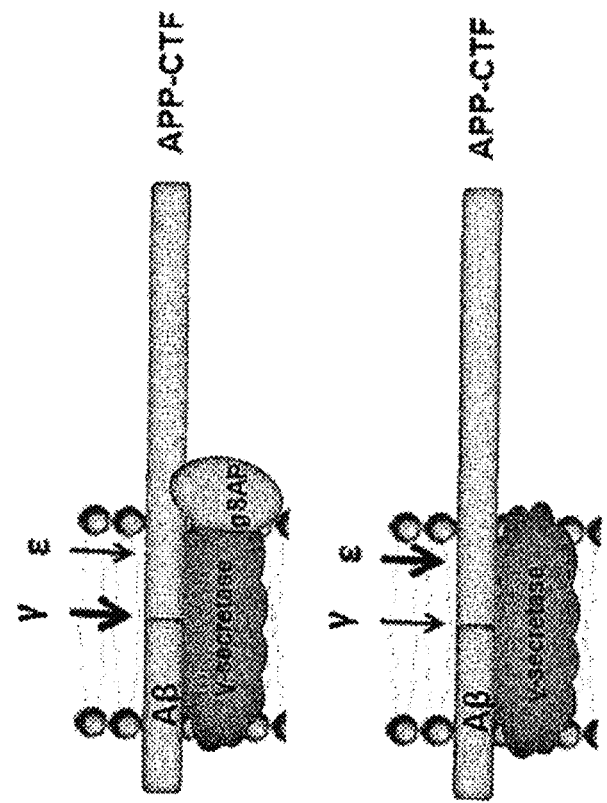
FIG. 5 shows gSAP action on APP processing. Ternary complex of gSAP, APP and γ-secretase (top) is associated with elevated γ-cleavage (Aβ-beta production) and reduced ε-cleavage (AICD production). In the absence of gSAP (bottom), the binary complex of APP and ε-secretase is associated with decreased γ-cleavage and increased ε-cleavage.

Intrahippocampal injection of AAV2-carrying shRNA against gSAP reduces amyloid plaque development in double transgenic AD mice. Areas showing GFP staining indicate regions of AAV2 vector expression, while red fluorescence reveals amyloid plaques, showing that the vector expression coincides with the reduction in plaque formation. GFP-positive regions from five consecutive sections are analyzed by confocal microscopy. Data is expressed as plaques per $mm^2$ (n=4. ***: P<0.001) (FIG. 4).

Example 12

N-(6-methyl-5-(4-phenylpyrimidin-2-ylamino)pyridin-3-yl)-4-((1-methylpiperidin-4-yl)methyl)benzamide binds gSAP and lowers Aβ

N-(6-methyl-5-(4-phenylpyrimidin-2-ylamino)pyridin-3-yl)-4-((1-methylpiperidin-4-yl)methyl)benzamide (WO/2008/153974, ex. 7) is selected as a representative imatinib analogue having little kinase inhibitory activity when tested against a panel of 40 kinases (data not shown). Compared to imatinib, which has a $K_1$ versus Abl kinase (its principal target for approved anti-cancer indications) of roughly 100 nM, N-(6-methyl-5-(4-phenylpyrimidin-2-ylamino)pyridin-3-yl)-4-((1-methylpiperidin-4-yl)methyl)benzamide has 100-fold weaker activity, approximately 12,000 nM Ki versus this kinase. This compound nevertheless inhibits Aβ in a manner similar to imatinib. This further supports that the kinase inhibitory activity of imatinib is not the basis for its activity against gSAP but rather that it has a specific effect on the interaction between gSAP and gamma secretase.

HEK293 cells are transfected with gSAP with a C-terminal Hemaglutinin (HA) tag. A membrane pellet is prepared the pellet and resuspended in 50 mM Hepes, 150 mM NaCl, 5 mM MgCl2, 5 mM CaCl2, and incubated with the indicated amount of either imatinib or N-(6-methyl-5-(4-phenylpyrimidin-2-ylamino)pyridin-3-yl)-4-((1-methylpiperidin-4-yl)methyl)benzamide for 2 hrs, followed by addition of 2 uM Biotin-NCG and incubated for 1 hr. The membrane is pelleted down, solubilized in 50 mM Hepes, 150 mM NaCl, 1% octyl β-D-glucopyranoside, and bound to Myone streptavidin T1 beads for 1 hr, then washed 3 times. The captured protein is released by incubation with SDS sample buffer and detected by western blot.

Total human Aβ in the N2a cell system is measured in a standard sandwich ELISA by using a specific monoclonal antibody (6E10, Signet Laboratories) to capture the Aβ40 and Aβ42 and an antibody to Aβ17-24 (4G8, Signet Laboratories, Dedham, Mass.) for detection. Cell culture medium (5 μL/well) is diluted to 100 μL in phosphate-buffered saline/0.2% Tween 20 and loaded onto ELISA plates. For Western blot assays, cell medium is diluted with 2× tricine sodium dodecyl sulfate sample buffer, and heated at 95° C. for 5 min. Aβ is separated by electrophoresis on 16% tricine polyacrylamide gels (BioRad), proteins are transferred onto nitrocellulose membranes and blocked overnight with LiCor blocking buffer (LiCor, Lincoln, Nebr.). Aβ is detected with antibody 4G8 and an Alexa 680-conjugated rabbit anti-mouse secondary and scanned with a LiCor Odyssey infrared scanner. N-(6-methyl-5-(4-phenylpyrimidin-2-ylamino)pyridin-3-yl)-4-((1-methylpiperidin-4-yl)methyl)benzamide significantly lowers Aβ at concentrations of <500 nM.

For detection of Notch cleavage, HEK293 human embryonic kidney cells are transfected with mouse ΔE-Notch cDNA with a C-terminal myc tag. For analysis of ΔE-Notch cleavage, cells are incubated with test compounds for 4 h. Cell extracts are prepared by lysing cells in cell lysis buffer (50 mM Tris, pH7.5, 10 mM NaCl, 5 mM EGTA, 1 mM EDTA and complete protease inhibitors (Roche Diagnostics, Indianapolis, Ind.). Protein concentration is determined using Bradford protein detection reagent. Volume is adjusted with cell lysis buffer, then 4× sample loading buffer (Tris-Tricine gel loading buffer) is added, samples are heated 5 min at 95° C., and equivalent amounts of cell protein for each treatment are loaded onto a 10% Bis-Tris gel. C-terminal Notch species are detected with monoclonal anti-c-myc antibody 9E10 (Roche Diagnostics) and fluorescent goat anti-mouse secondary antibody. Fluorescent antibody is quantitated via LiCor Odyssey infrared fluorescence detector.

N-(6-methyl-5-(4-phenylpyrimidin-2-ylamino)pyridin-3-yl)-4-((1-methylpiperidin-4-yl)methyl)benzamide and imatinib do not influence NOTCH metabolism in the cell system outlined. The competitive and direct gamma-secretase inhibitor DAPT is used as a positive control in the assay. Since inhibition of NOTCH processing could potentially cause undesirable side-effects, compounds that prevent processing of NOTCH are less desirable as drug candidates. N-(6-methyl-5-(4-phenylpyrimidin-2-ylamino)pyridin-3-yl)-4-((1-methylpiperidin-4-yl)methyl)benzamide is comparable to imatinib in this assay.

Example 13

Synthesis of N-(6-methyl-5-(4-phenylpyrimidin-2-ylamino)pyridin-3-yl)-4-((1-methylpiperidin-4-yl)methyl)benzamide N-(6-methyl-5-(4-phenylpyrimidin-2-ylamino)pyridin-3-yl)-4-((1-methylpiperidin-4-yl)methyl)benzamide, depicted below, is disclosed in WO/2008/153974, but a synthesis is provided for convenience sake:

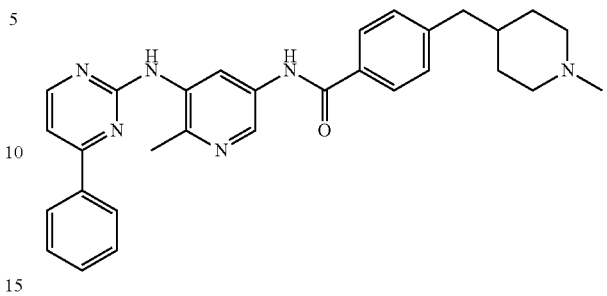

a) (2-Methyl-5-nitro-pyridin-3-yl)-(4-phenyl-pyrimidin-2-yl)-amine

To a mixture of 3-Bromo-2-methyl-5-nitro-pyridine (4.46 g, 2.10 mmol) and 4-Phenyl-2-pyrimidinamine (1.3 g, 1.75 mmol) in thy toluene (25 mL) are added Cs$_2$CO$_3$ (0.85 g, 2.62 mmol), Pd$_2$(dba)$_3$ (32 mg, 0.035 mmol) and Xantphos (60 mg, 0.105 mmol). The mixture is evacuated and purged with N$_2$, heated to 90° C. under nitrogen for 24 h. The reaction mixture is cooled to room temperature, diluted with EtOAc and filtered. The filtrate is concentrated under reduced pressure, and the residue is purified by silica gel column chromatography to afford product as yellow solids (320 mg, yield 59%). $^1$H NMR (200 MHz, CDCl$_3$): δ 2.75 (s, 3H), 7.19 (s, 1H), 7.37 (d, J=4.0 Hz, 1H), 7.57-7.54 (m, 3H), 8.17-8.12 (m, 2H), 8.59 (d, J=4.0 Hz, 1H), 9.02 (d, J=2.0 Hz, 1H), 9.87 (d, J=2.0 Hz, 1H); MS ESI$^+$) m/z 308 [M+H]$^+$.

(b) 2-methyl-N$^3$-(4-phenylpyrimidin-2-yl)pyridine-3,5-diamine

A mixture of catalytic ferric chloride (12 mg), (2-Methyl-5-nitro-pyridin-3-yl)-(4-phenyl-pyrimidin-2-yl)-amine (320 mg, 1.04 mmol) in hydrazine hydrate (12 mL) and methanol (20 mL) is refluxed for 15 min. The reaction mixture is cooled to room temperature, concentrated under reduced pressure and the crude residue is dissolved in water and extracted with EtOAc. The combined extracts are dried over anhydrous Na$_2$SO$_4$, filtered, concentrated under reduced pressure. The residue is stirred with Et$_2$O for 5 minutes, the ether layer is decanted and the residue is dried under vacuum to give product as yellow solids (270 mg, yield 93%). Mp: 133.1-133.4° C.; $^1$H NMR (200 MHz, CDCl$_3$): δ 2.51 (s, 3H), 3.62 (bs, 2H), 6.93 (s, 1H), 7.20 (d, J=6.0 Hz, 1H), 7.52-7.49 (m, 3H), 7.74 (d, J=2.0 Hz, 1H), 8.08-8.03 (m, 2H), 8.13 (d, J=2.4 Hz, 1H), 8.48 (d, J=4.0 Hz, 1H); MS (ESI$^+$) m/z 278 [M+H]$^+$.

(c) 4-((1-methylpiperidin-4-yl)methyl)benzoic acid 4-(piperidin-4-ylmethyl)benzoic acid (114 mg, 0.342 mmol) is dissolved in 2 mL of methanol, and then 37% formaldehyde aqueous solution (56 μL, 0.685 mmol) is added. The reaction mixture is stirred at room temperature for 5 min, and then NaBH$_3$CN (26 mg, 0.41 mmol) is added. The mixture is stirred at room temperature for 2 h, quenched with a small amount of water, and then evaporated to dryness under high vacuum to give white foamy solids, which is used for the next reaction without further purification. MS (ESC) m/z 234.1 [M+H]+.

d) N-(6-methyl-5-(4-phenylpyrimidin-2-ylamino) pyridin-3-yl)-4-((1-methylpiperidin-4-yl)methyl) benzamide DIEA (149 μL, 0.86 mmol) is added into a suspension of 2-methyl-N³-(4-phenylpyrimidin-2-yl)pyridine-3,5-diamine (47 mg, 0.17 mmol), 4-((1-methylpiperidin-4-yl)methyl) benzoic acid (40 mg, 0.17 mmol), BOP (91 mg, 0.21 mmol) in DMF. The reaction mixture is stirred at room temperature under argon atmosphere overnight. The mixture is filtered through a 0.45 μm microfilter and the filtrate is purified by a Waters semi-preparative HPLC to give 16 mg of the final product as white powder. MS (ESI+) m/z 493.1 [M+H]+.

Temperatures are given in degrees Celsius (° C.); operations are carried out at room or ambient temperature ("rt") are at a temperature in the range of 18-25° C. Organic solutions are dried over anhydrous sodium sulphate; evaporation of solvent is carried out using a rotary evaporator under reduced pressure (600-4000 Pascals; 4.5-30 mmHg) with a bath temperature of up to 60° C. In general, the course of reactions is followed by TLC and reaction times are given for illustration only; final products had satisfactory proton nuclear magnetic resonance (NMR) spectra and/or mass spectral data. Yields are given for illustration only and are not necessarily those which can be obtained by diligent process development; preparations are repeated if more material is required. When given, NMR data is in the form of delta values for major diagnostic protons, given in parts per million (ppm) relative to tetramethylsilane (TMS) as an internal standard. Chemical symbols have their usual meanings; SI units and symbols are used. The following abbreviations have been used:

Cs₂CO₃ cesium carbonate;
HPLC high performance liquid chromatography;
Na₂SO₄ sodium sulfate;
NaBH₃CN sodium cyanoborohydride
BOP benzotriazol-1-yloxytris(dimethylamino)phosphonium hexafluorophosphate;
DMF N,N-dimethylformamide;
EtOAc ethyl acetate;
DIEA N,N-diisopropylethylamine;
Pd₂(dba)₃ tris(dibenzylideneacetone)dipalladium(0); and
Xantphos 4,5-Bis(diphenylphosphino)-9,9-dimethylxanthene

Example 15

Binding Assay

In one example, an assay may be used to test for an inhibitor of the gSAP protein. A selected sequence of the gSAP protein may be used to detect binding with a potential inhibitor.

Example 16

Diagnostic Assays a. A diagnostic assay is used to measure levels of the gSAP protein. Elevated levels of the gSAP protein may be correlated with disease.

b. Genetic analysis of variants in the gSAP region is used to identify candidates for therapy targeting gSAP. Nine SNPs in the region of the gene for gSAP are identified (PION). In single marker analyses, none of the SNPs is associated with AD after correction for multiple testing. However, in sliding window haplotype analyses, 4 haplotypes are associated with AD:
  a) rs6976567|rs1468682|rs1819814,
  b) rs1468682|rs1819814|rs4729535,
  c) rs1819814|rs4729535|rs4729540,
  d) rs7781642|rs6955503|rs7776973

Two of the SNPs in these haplotypes (rs4729540 and rs7776973) are significantly associated with delayed recognition test in the single marker analyses also. Patients identified as having these haplotypes are thus candidates for treatment with gSAP inhibitors.

Example 17

Identification of Region of Interaction Between gSAP and APP

Alternative combinations and variations of the examples provided will become apparent based on this disclosure. It is not possible to provide specific examples for all of the many possible combinations and variations of the embodiments described, but such combinations and variations may be claims that eventually issue.

---

The invention claimed is:

1. A method for inhibiting the accumulation of abnormal protein aggregates in a warm-blooded animal in need of such inhibition which comprises:

Measuring gSAP ("gamma secretase activating protein") expression for identifying whether the animal in need thereof has elevated expression levels and/or mutations in gSAP, wherein the animal in need thereof has elevated expression levels and/or mutations in gSAP relative to normal values as identified using a control population; and administering to said animal an effective amount of a compound to inhibit gSAP activity, wherein the mutations are one or more haplotypes selected from the following groups of SNPs:
a) rs6976567|rs1468682|rs1819814,
b) rs1468682|rs1819814|rs4729535,
c) rs1819814|rs4729535|rs4729540, and
d) rs7781642|rs6955503|rs7776973, and wherein the compound to inhibit gSAP activity is selected from imatinib or a labeled derivative thereof, inhibitory RNA molecules capable of inhibiting gSAP expression, vectors and cells producing said inhibitory RNA molecules, antibodies to gSAP, and vaccines for gSAP.

2. The method of claim 1, wherein the accumulation of abnormal protein aggregates is related to an Aβ-mediated disease, wherein the Aβ-mediated disease is selected from the group consisting of: Alzheimer's disease, memory and cognitive disorders, dementia, amyloid neuropathies, brain inflammation, nerve and brain trauma, vascular amyloidosis, and cerebral hemorrhage with amyloidosis.

3. The method of claim 1, wherein the mutations are one or more haplotypes selected from:
c) rs1819814|rs4729535|rs4729540 and
d) rs7781642|rs6955503|rs7776973.

* * * * *

SEQUENCE LISTING

```
<160> NUMBER OF SEQ ID NOS: 8

<210> SEQ ID NO 1
<211> LENGTH: 854
<212> TYPE: PRT
<213> ORGANISM: Homo sapiens

<400> SEQUENCE: 1

Met Ala Leu Arg Leu Val Ala Asp Phe Asp Leu Gly Lys Asp Val Leu
1               5                   10                  15

Pro Trp Leu Arg Ala Gln Arg Ala Val Ser Glu Ala Ser Gly Ala Gly
            20                  25                  30

Ser Gly Gly Ala Asp Val Leu Glu Asn Asp Tyr Glu Ser Leu His Val
        35                  40                  45

Leu Asn Val Glu Arg Asn Gly Asn Ile Ile Tyr Thr Tyr Lys Asp Asp
    50                  55                  60
```

```
Lys Gly Asn Val Val Phe Gly Leu Tyr Asp Cys Gln Thr Arg Gln Asn
 65                  70                  75                  80

Glu Leu Leu Tyr Thr Phe Glu Lys Asp Leu Gln Val Phe Ser Cys Ser
             85                  90                  95

Val Asn Ser Glu Arg Thr Leu Leu Ala Ala Ser Leu Val Gln Ser Thr
        100                 105                 110

Lys Glu Gly Lys Arg Asn Glu Leu Gln Pro Gly Ser Lys Cys Leu Thr
    115                 120                 125

Leu Leu Val Glu Ile His Pro Val Asn Asn Val Lys Val Leu Lys Ala
130                 135                 140

Val Asp Ser Tyr Ile Trp Val Gln Phe Leu Tyr Pro His Ile Glu Ser
145                 150                 155                 160

His Pro Leu Pro Glu Asn His Leu Leu Leu Ile Ser Glu Glu Lys Tyr
                165                 170                 175

Ile Glu Gln Phe Arg Ile His Val Ala Gln Glu Asp Gly Asn Arg Val
            180                 185                 190

Val Ile Lys Asn Ser Gly His Leu Pro Arg Asp Arg Ile Ala Glu Asp
        195                 200                 205

Phe Val Trp Ala Gln Trp Asp Met Ser Glu Gln Arg Leu Tyr Tyr Ile
210                 215                 220

Asp Leu Lys Lys Ser Arg Ser Ile Leu Lys Cys Ile Gln Phe Tyr Ala
225                 230                 235                 240

Asp Glu Ser Tyr Asn Leu Met Phe Glu Val Pro Leu Asp Ile Ser Leu
                245                 250                 255

Ser Asn Ser Gly Phe Lys Leu Val Asn Phe Gly Cys Asp Tyr His Gln
            260                 265                 270

Tyr Arg Asp Lys Phe Ser Lys His Leu Thr Leu Cys Val Phe Thr Asn
        275                 280                 285

His Thr Gly Ser Leu Cys Val Cys Tyr Ser Pro Lys Cys Ala Ser Trp
290                 295                 300

Gly Gln Ile Thr Tyr Ser Val Phe Tyr Ile His Lys Gly His Ser Lys
305                 310                 315                 320

Thr Phe Thr Thr Ser Leu Glu Asn Val Gly Ser His Met Thr Lys Gly
                325                 330                 335

Ile Thr Phe Leu Asn Leu Asp Tyr Tyr Val Ala Val Tyr Leu Pro Gly
            340                 345                 350

His Phe His Leu Leu Asn Val Gln His Pro Asp Leu Ile Cys His
        355                 360                 365

Asn Leu Phe Leu Thr Gly Asn Asn Glu Met Ile Asp Met Leu Pro His
        370                 375                 380

Cys Pro Leu Gln Ser Leu Ser Gly Ser Leu Val Leu Asp Cys Cys Ser
385                 390                 395                 400

Gly Lys Leu Tyr Arg Ala Leu Leu Ser Gln Ser Ser Leu Leu Gln Leu
                405                 410                 415

Leu Gln Asn Thr Cys Leu Asp Cys Glu Lys Met Ala Ala Leu His Cys
            420                 425                 430

Ala Leu Tyr Cys Gly Gln Gly Ala Gln Phe Leu Glu Ala Gln Ile Ile
        435                 440                 445

Gln Trp Ile Ser Glu Asn Val Ser Ala Cys His Ser Phe Asp Leu Ile
    450                 455                 460

Gln Glu Phe Ile Ile Ala Ser Ser Tyr Trp Ser Val Tyr Ser Glu Thr
465                 470                 475                 480
```

```
Ser Asn Met Asp Lys Leu Leu Pro His Ser Ser Val Leu Thr Trp Asn
                485                 490                 495

Thr Glu Ile Pro Gly Ile Thr Leu Val Thr Glu Asp Ile Ala Leu Pro
            500                 505                 510

Leu Met Lys Val Leu Ser Phe Lys Gly Tyr Trp Glu Lys Leu Asn Ser
            515                 520                 525

Asn Leu Glu Tyr Val Lys Tyr Ala Lys Pro His Phe His Tyr Asn Asn
            530                 535                 540

Ser Val Val Arg Arg Glu Trp His Asn Leu Ile Ser Glu Glu Lys Thr
545                 550                 555                 560

Gly Lys Arg Arg Ser Ala Ala Tyr Val Arg Asn Ile Leu Asp Asn Ala
                565                 570                 575

Val Lys Val Ile Ser Asn Leu Glu Ala Arg Asn Leu Gly Pro Arg Leu
            580                 585                 590

Thr Pro Leu Leu Gln Glu Glu Asp Ser His Gln Arg Leu Leu Met Gly
            595                 600                 605

Leu Met Val Ser Glu Leu Lys Asp His Phe Leu Arg His Leu Gln Gly
            610                 615                 620

Val Glu Lys Lys Lys Ile Glu Gln Met Val Leu Asp Tyr Ile Ser Lys
625                 630                 635                 640

Leu Leu Asp Leu Ile Cys His Ile Val Glu Thr Asn Trp Arg Lys His
                645                 650                 655

Asn Leu His Ser Trp Val Leu His Phe Asn Ser Arg Gly Ser Ala Ala
                660                 665                 670

Glu Phe Ala Val Phe His Ile Met Thr Arg Ile Leu Glu Ala Thr Asn
            675                 680                 685

Ser Leu Phe Leu Pro Leu Pro Pro Gly Phe His Thr Leu His Thr Ile
690                 695                 700

Leu Gly Val Gln Cys Leu Pro Leu His Asn Leu Leu His Cys Ile Asp
705                 710                 715                 720

Ser Gly Val Leu Leu Leu Thr Glu Thr Ala Val Ile Arg Leu Met Lys
                725                 730                 735

Asp Leu Asp Asn Thr Glu Lys Asn Glu Lys Leu Lys Phe Ser Ile Ile
                740                 745                 750

Val Arg Leu Pro Pro Leu Ile Gly Gln Lys Ile Cys Arg Leu Trp Asp
            755                 760                 765

His Pro Met Ser Ser Asn Ile Ile Ser Arg Asn His Val Thr Arg Leu
            770                 775                 780

Leu Gln Asn Tyr Lys Lys Gln Pro Arg Asn Ser Met Ile Asn Lys Ser
785                 790                 795                 800

Ser Phe Ser Val Glu Phe Leu Pro Leu Asn Tyr Phe Ile Glu Ile Leu
                805                 810                 815

Thr Asp Ile Glu Ser Ser Asn Gln Ala Leu Tyr Pro Phe Glu Gly His
            820                 825                 830

Asp Asn Val Asp Ala Glu Phe Val Glu Glu Ala Ala Leu Lys His Thr
            835                 840                 845

Ala Met Leu Leu Gly Leu
    850

<210> SEQ ID NO 2
<211> LENGTH: 808
<212> TYPE: PRT
<213> ORGANISM: Canis familiaris

<400> SEQUENCE: 2
```

-continued

```
Met Thr Gln Asn Leu Ser Trp Pro Gly His Ser Asn Gly Ser Cys
1               5                   10                  15

Ile Arg Phe Pro Val Ala Gly Gly Thr Ala Val Leu Trp Gln Gly Ala
                20                  25                  30

Val Ser Ser Ile Gln Gly Leu Gly Thr Ala Asp His Glu Leu Pro Thr
            35                  40                  45

Trp Arg Ala Tyr Glu Gln Leu Pro Tyr Ala Asp Leu Ala Ser Val Asp
    50                  55                  60

Leu Cys Ile Gln Leu Leu Ile Pro Phe Ala Phe Ile Pro Thr Gly Ser
65                  70                  75                  80

Lys Cys Leu Thr Leu Leu Val Glu Ile His Pro Val Asn Asn Val Lys
                85                  90                  95

Val Leu Lys Ala Val Asp Ser Ser Ile Trp Val Gln Phe Leu Tyr Pro
            100                 105                 110

Gln Val Glu Ser His Pro Pro Glu Asn His Leu Leu Leu Ile Ser
                115                 120                 125

Glu Glu Lys Tyr Ile Glu Lys Phe His Ile His Val Ile Gln Glu Asp
            130                 135                 140

Gly Asn Lys Val Val Leu Arg Asp Ser Gly His Leu Pro Arg Glu Arg
145                 150                 155                 160

Val Ala Glu Asp Phe Val Trp Ala Gln Trp Asp Met Ser Glu Gln Arg
                165                 170                 175

Leu Tyr Tyr Ile Val Leu Lys Lys Ser Arg Ser Ile Leu Lys Cys Ile
            180                 185                 190

Gln Phe Ser Ala Asn Glu Lys Phe Asn Leu Met Phe Glu Ala Pro Leu
            195                 200                 205

Asp Ile Thr Leu Ser Ala Ser Gly Phe Glu Leu Val Asn Phe Gly Cys
210                 215                 220

Asp Asp Leu Gln Asp Gln Gly Asn Leu Ser Lys His Leu Thr Leu Cys
225                 230                 235                 240

Val Phe Thr Asn His Thr Gly Ser Leu Cys Val Cys Tyr Ser Pro Lys
                245                 250                 255

Phe Asp Ser Trp Glu Lys Ile Thr Tyr Ser Val Phe Tyr Phe His Lys
                260                 265                 270

Gly His Ser Lys Thr Phe Thr Ala Ala Leu Gly Ser Val Asp Ser Leu
            275                 280                 285

Val Thr Lys Gly Leu Thr Phe Leu Asn Leu Asp Tyr Tyr Val Ala Val
            290                 295                 300

Tyr Leu Pro Gly His Phe His Leu Leu Asn Ile Gln His Pro Asp
305                 310                 315                 320

Leu Ile Cys His Ser Leu Phe Leu Thr Gly Asn Asn Glu Val Val Asp
                325                 330                 335

Met Leu Pro His Ser Pro Leu Gln Ser Leu Gly Ser Leu Val Leu
                340                 345                 350

Asp Trp Cys Ser Gly Lys Leu Tyr Arg Ala Leu Leu Asn Gln Ser Tyr
                355                 360                 365

Leu Leu Gln Phe Leu Trp Asn Thr Gln Leu Asp Cys Glu Lys Met Ala
    370                 375                 380

Val Leu His Cys Val Leu Ser Cys Gly Arg Asp Pro Arg Phe Leu Glu
385                 390                 395                 400

Ala Lys Ile Ile Gln Trp Ile Ser Glu Asn Ile Ser Thr Cys His Ser
                405                 410                 415
```

```
Phe Asp Leu Ile Gln Glu Phe Ile Ile Ala Ser Ser Tyr Trp Ser Ile
                420                 425                 430

Tyr Pro Glu Thr Ser Asn Ile Asp Lys Leu Leu Pro Tyr Ser Ser Val
                435                 440                 445

Leu Thr Trp Asn Thr Glu Ile Pro Gly Ile Thr Leu Val Thr Glu Glu
            450                 455                 460

Ile Thr Leu Pro Phe Met Lys Val His Ser Phe Lys Gly Tyr Trp Glu
465                 470                 475                 480

Lys Leu Asn Ser Asn Leu Glu Tyr Val Lys Cys Ser Lys Pro Cys Leu
                485                 490                 495

Leu Tyr Asn Asn Ser Met Val Lys Arg Glu Trp His Ser Leu Ile Ser
            500                 505                 510

Glu Glu Lys Thr Gly Arg Arg Ser Met Val Tyr Val Arg Asn Ile
                515                 520                 525

Phe Asp Asn Ala Met Lys Val Ile Ser Asn Leu Glu Ala Arg Asn Leu
                530                 535                 540

Glu Pro Arg Leu Thr Pro Leu Phe Gln Glu Glu Asp Tyr His Gln Arg
545                 550                 555                 560

Leu Leu Ile Gly Leu Met Val Ser Glu Leu Arg Glu His Leu Leu Arg
                565                 570                 575

His Leu Gln Gly Ile Gly Lys Lys Ile Glu Gln Met Val Leu Asp
            580                 585                 590

Tyr Ile Ser Lys Leu Leu Asp Leu Ile Cys Gln Ile Leu Glu Thr Ser
                595                 600                 605

Trp Arg Thr His His Leu His Pro Trp Val Leu His Leu Arg Ala Ser
610                 615                 620

Ala Ala Glu Phe Thr Val Phe His Ile Met Thr Arg Ile Leu Glu Ala
625                 630                 635                 640

Thr Met Ser Leu Phe Leu Pro Leu Pro Pro Gly Phe His Thr Leu His
                645                 650                 655

Thr Ile Leu Gly Val His Cys Leu Pro Leu His Asn Leu Leu His Tyr
            660                 665                 670

Ile Asp Ser Gly Val Leu Leu Leu Thr Glu Thr Ala Val Ile Arg Leu
                675                 680                 685

Met Lys Asp Leu Asp Asn Ser Glu Asn Asn Glu Lys Leu Lys Phe Ser
690                 695                 700

Ile Ile Val Arg Leu Pro Pro His Ile Gly Gln Lys Ile Cys Arg Leu
705                 710                 715                 720

Trp Asp His Pro Met Ser Ser Asn Ile Ile Ser Arg Asn His Val Lys
                725                 730                 735

Gln Leu Leu Leu Asn Tyr Lys Lys Gln Pro Gln Ser Ser Met Ile Asp
            740                 745                 750

Lys Ser Pro Gly Ser Val Glu Phe Leu Pro Leu Asn Tyr Phe Ile Glu
                755                 760                 765

Ile Leu Thr Asp Ile Glu Ser Ser Asn Gln Ala Leu Tyr Ala Phe Glu
                770                 775                 780

Gly His Asp Asn Val Asp Ala Lys Phe Val Glu Glu Ala Ala Leu Lys
785                 790                 795                 800

His Thr Thr Met Leu Leu Gly Leu
                805
```

<210> SEQ ID NO 3
<211> LENGTH: 854
<212> TYPE: PRT

<213> ORGANISM: Bos primigenius

<400> SEQUENCE: 3

| | | | | | | | | | | | | | | |
|---|---|---|---|---|---|---|---|---|---|---|---|---|---|---|
| Met | Ala | Leu | Arg | Leu | Ile | Ala | Asp | Phe | Asp | Leu | Glu | Lys | Asp | Val | Leu |
| 1 | | | | 5 | | | | | 10 | | | | | 15 | |

| Pro | Trp | Leu | Arg | Val | Gln | Leu | Ala | Ala | Ser | Ala | Ala | Gly | Ala | Arg |
|---|---|---|---|---|---|---|---|---|---|---|---|---|---|---|
| | | | 20 | | | | | 25 | | | | | 30 | |

| Gly | Gly | Gly | Pro | Gly | Val | Leu | Glu | Asn | Asn | Tyr | Glu | Cys | Leu | Arg | Val |
|---|---|---|---|---|---|---|---|---|---|---|---|---|---|---|---|
| | | 35 | | | | | 40 | | | | | 45 | | | |

| Leu | Asn | Val | Glu | Arg | Asn | Arg | Asn | Ile | Ile | Tyr | Thr | Tyr | Lys | Asp | Asn |
|---|---|---|---|---|---|---|---|---|---|---|---|---|---|---|---|
| | 50 | | | | | 55 | | | | | 60 | | | | |

| Lys | Gly | Asn | Val | Phe | Phe | Gly | Leu | Tyr | Asp | Tyr | Gln | Thr | Lys | Gln | Asn |
|---|---|---|---|---|---|---|---|---|---|---|---|---|---|---|---|
| 65 | | | | | 70 | | | | | 75 | | | | | 80 |

| Glu | His | Leu | Tyr | Thr | Phe | Glu | Lys | Asp | Leu | Gln | Val | Val | Ser | Cys | Ser |
|---|---|---|---|---|---|---|---|---|---|---|---|---|---|---|---|
| | | | | 85 | | | | | 90 | | | | | 95 | |

| Val | Asn | Lys | Glu | Lys | Thr | Leu | Leu | Ala | Thr | Ser | Leu | Val | Gln | Ala | Ala |
|---|---|---|---|---|---|---|---|---|---|---|---|---|---|---|---|
| | | | 100 | | | | | 105 | | | | | 110 | | |

| Lys | Glu | Gly | Arg | Ser | Asn | Glu | Leu | Gln | Pro | Gly | Ser | Lys | Cys | Leu | Thr |
|---|---|---|---|---|---|---|---|---|---|---|---|---|---|---|---|
| | | | 115 | | | | | 120 | | | | | 125 | | |

| Leu | Leu | Val | Glu | Ile | His | Pro | Ile | Asn | Asn | Val | Lys | Val | Leu | Lys | Ala |
|---|---|---|---|---|---|---|---|---|---|---|---|---|---|---|---|
| | 130 | | | | | 135 | | | | | 140 | | | | |

| Val | Asp | Ser | Tyr | Ile | Trp | Val | Gln | Phe | Leu | Tyr | Pro | His | Val | Glu | Ser |
|---|---|---|---|---|---|---|---|---|---|---|---|---|---|---|---|
| 145 | | | | | 150 | | | | | 155 | | | | | 160 |

| Cys | Pro | Gln | Pro | Lys | Asn | His | Leu | Leu | Leu | Ser | Glu | Glu | Lys | Tyr |
|---|---|---|---|---|---|---|---|---|---|---|---|---|---|---|
| | | | | 165 | | | | | 170 | | | | | 175 |

| Ile | Glu | Gln | Phe | His | Ile | Gln | Val | Val | Gln | Asp | Gly | Asn | Arg | Val |
|---|---|---|---|---|---|---|---|---|---|---|---|---|---|---|
| | | | 180 | | | | | 185 | | | | | 190 | |

| Val | Ile | Lys | Asn | Ser | Gly | His | Leu | Pro | Arg | Glu | Arg | Ile | Ala | Glu | Asp |
|---|---|---|---|---|---|---|---|---|---|---|---|---|---|---|---|
| | | 195 | | | | | 200 | | | | | 205 | | | |

| Phe | Val | Trp | Ala | Gln | Trp | Asp | Met | Ser | Glu | Gln | Arg | Leu | Tyr | Tyr | Ile |
|---|---|---|---|---|---|---|---|---|---|---|---|---|---|---|---|
| | 210 | | | | | 215 | | | | | 220 | | | | |

| Asp | Leu | Lys | Lys | Ser | Arg | Ser | Val | Leu | Lys | Cys | Ile | Gln | Phe | Tyr | Ala |
|---|---|---|---|---|---|---|---|---|---|---|---|---|---|---|---|
| 225 | | | | | 230 | | | | | 235 | | | | | 240 |

| Glu | Glu | His | Phe | Asn | Leu | Met | Phe | Glu | Ala | Pro | Leu | Asp | Ile | Ser | Leu |
|---|---|---|---|---|---|---|---|---|---|---|---|---|---|---|---|
| | | | | 245 | | | | | 250 | | | | | 255 | |

| Ser | Asp | Ser | Gly | Phe | Lys | Leu | Val | Asn | Phe | Gly | Tyr | Ser | Asp | Leu | Gln |
|---|---|---|---|---|---|---|---|---|---|---|---|---|---|---|---|
| | | | 260 | | | | | 265 | | | | | 270 | | |

| Asp | Lys | Glu | Glu | Leu | Ser | Glu | His | Leu | Thr | Leu | Cys | Val | Phe | Thr | Asn |
|---|---|---|---|---|---|---|---|---|---|---|---|---|---|---|---|
| | 275 | | | | | 280 | | | | | 285 | | | | |

| His | Thr | Gly | Ser | Leu | Cys | Val | Cys | Tyr | Cys | Pro | Asn | Phe | Asp | Ser | Trp |
|---|---|---|---|---|---|---|---|---|---|---|---|---|---|---|---|
| | 290 | | | | | 295 | | | | | 300 | | | | |

| Glu | Gln | Ile | Thr | Tyr | Ser | Val | Phe | Tyr | Phe | His | Lys | Gly | His | Ser | Lys |
|---|---|---|---|---|---|---|---|---|---|---|---|---|---|---|---|
| 305 | | | | | 310 | | | | | 315 | | | | | 320 |

| Thr | Phe | Thr | Thr | Thr | Leu | Gly | Ser | Val | Asp | Ser | His | Val | Thr | Lys | Gly |
|---|---|---|---|---|---|---|---|---|---|---|---|---|---|---|---|
| | | | | 325 | | | | | 330 | | | | | 335 | |

| Ile | Thr | Phe | Leu | Asn | Leu | Asp | Tyr | Tyr | Val | Ala | Val | Tyr | Leu | Pro | Gly |
|---|---|---|---|---|---|---|---|---|---|---|---|---|---|---|---|
| | | | 340 | | | | | 345 | | | | | 350 | | |

| His | Phe | Phe | His | Leu | Leu | Asn | Ile | Gln | His | Pro | Asp | Leu | Ile | Cys | His |
|---|---|---|---|---|---|---|---|---|---|---|---|---|---|---|---|
| | | | 355 | | | | | 360 | | | | | 365 | | |

| Ser | Leu | Phe | Leu | Thr | Glu | Asn | Ser | Glu | Val | Ile | Asp | Met | Leu | Pro | His |
|---|---|---|---|---|---|---|---|---|---|---|---|---|---|---|---|
| | 370 | | | | | 375 | | | | | 380 | | | | |

| Ser | Pro | Leu | Gln | Ser | Leu | Ser | Gly | Ser | Leu | Val | Leu | Asp | Ser | Arg | Ser |
|---|---|---|---|---|---|---|---|---|---|---|---|---|---|---|---|
| 385 | | | | | 390 | | | | | 395 | | | | | 400 |

-continued

```
Gly Lys Leu Tyr Arg Val Leu Leu Asn Gln Ser Tyr Leu Val Glu Phe
                405                 410                 415
Leu Arg Ser Ala Arg Leu Asp Cys Glu Arg Met Ala Leu Leu His Cys
            420                 425                 430
Ala Leu Ser His Gly Arg Asp Pro Arg Leu Glu Ala Lys Ile Ile
        435                 440                 445
Gln Trp Ile Ser Glu Asn Ile Ser Ala Cys His Ser Phe Asp Leu Ile
    450                 455                 460
Gln Glu Phe Ile Ile Ala Ser Ser Tyr Trp Ser Ile Tyr Pro Glu Thr
465                 470                 475                 480
Ser Asn Met Asp Lys Leu Leu Pro Tyr Ser Ser Leu Leu Thr Trp Asp
                485                 490                 495
Thr Glu Ile Pro Gly Ile Thr Leu Val Thr Glu Glu Ile Pro Leu Pro
            500                 505                 510
Leu Met Lys Val His Ser Phe Lys Gly Tyr Trp Glu Lys Leu Asn Ser
        515                 520                 525
Asn Leu Glu Tyr Val Lys Tyr Ser Lys Pro His Leu His Tyr Asn Asn
    530                 535                 540
Ser Val Val Arg Arg Glu Trp His Asn Leu Ile Ser Glu Glu Lys Thr
545                 550                 555                 560
Gly Lys Arg Arg Ser Thr Val Tyr Val Arg Asn Ile Leu Asp Asn Ala
                565                 570                 575
Ile Lys Val Ile Ser Asn Val Glu Ala Lys Asn Leu Glu Pro Arg Leu
            580                 585                 590
Thr Pro Leu Phe Gln Glu Glu Asp Thr His Gln Gln Leu Leu Ile Gly
        595                 600                 605
Leu Met Val Ser Glu Leu Arg Glu His Leu Leu Arg His Leu Gln Gly
    610                 615                 620
Val Glu Lys Arg Lys Ile Glu Gln Met Val Leu Asp Tyr Val Ser Lys
625                 630                 635                 640
Leu Leu Asp Leu Ile Cys Gln Ile Leu Glu Ala Ser Trp Arg Lys His
                645                 650                 655
Asn Leu His Pro Trp Ala Leu His Phe Asn Arg Gln Ala Ser Ala Ala
            660                 665                 670
Glu Phe Ala Val Phe His Ile Met Thr Arg Ile Leu Glu Ala Thr Asn
        675                 680                 685
Thr Leu Phe Leu Pro Leu Pro Pro Gly Phe His Thr Leu His Met Ile
    690                 695                 700
Leu Gly Val Arg Cys Leu Pro Leu His Asn Leu Leu His Tyr Ile Asp
705                 710                 715                 720
His Gly Val Leu Leu Thr Glu Ala Ala Val Thr Arg Leu Met Lys
                725                 730                 735
Asp Leu Asp Asn Thr Glu Lys Asn Glu Lys Leu Lys Phe Ser Ile Ile
            740                 745                 750
Met Arg Leu Pro Pro Leu Thr Gly Gln Lys Ile Cys Arg Leu Trp Asp
        755                 760                 765
His Pro Val Ser Ser Asn Ile Ile Ser Arg Asn His Val Lys Arg Leu
    770                 775                 780
Leu Gln Asn Tyr Asn Lys Gln Pro Trp Ser Val Met Asp Lys Ser
785                 790                 795                 800
Ser Phe Ser Val Glu Phe Leu Pro Leu Asn Tyr Phe Ile His Ile Leu
                805                 810                 815
Thr Asp Ile Glu Ser Ser Asn Pro Ala Leu Tyr Ala Phe Glu Gly His
```

```
                       820                 825                 830
Asp Asn Val Asp Ala Lys Phe Val Glu Glu Ala Ala Leu Lys His Thr
                835                 840                 845

Ala Met Leu Leu Gly Leu
            850

<210> SEQ ID NO 4
<211> LENGTH: 858
<212> TYPE: PRT
<213> ORGANISM: Mus musculus

<400> SEQUENCE: 4

Met Ala Leu Arg Leu Val Thr His Phe Asp Val Leu Glu Asp Val Leu
1               5                   10                  15

Pro Ser Leu Leu Thr Gln Ala Ala Thr Thr Asp Glu Gly Asp Arg Ala
            20                  25                  30

Gly Val Leu Glu Thr Thr Tyr Gly Ser Leu Arg Val Leu Asn Ile Glu
        35                  40                  45

Arg Asn Gly Asn Ile Ile Tyr Thr Tyr Lys Asp Asn Lys Gly Asn Ala
    50                  55                  60

Val Phe Gly Leu Tyr Asp Cys Gln Thr Arg Gln Asn Glu His Leu Tyr
65                  70                  75                  80

Thr Phe Glu Lys Asp Met Gln Ala Val Ser Cys Ser Val Asn Ser Glu
                85                  90                  95

Arg Thr Val Leu Ala Ala Ser Phe Ile Gln Tyr Thr Thr Glu Gly Val
            100                 105                 110

Lys Asn Asp Leu Gln Pro Gly Ser Lys Cys Leu Thr Leu Leu Val Glu
        115                 120                 125

Ile His Pro Val Asn Asn Val Lys Val Leu Lys Ala Val Asp Ser Cys
    130                 135                 140

Val Trp Val Gln Phe Leu Tyr Pro Gln Ala Glu Ser His Leu Leu Pro
145                 150                 155                 160

Gln Asn His Leu Leu Leu Ile Ser Glu Glu Lys Tyr Ile Glu Arg Phe
                165                 170                 175

His Ile Gln Ile Thr Arg Glu Asp Gly Asp Arg Val Val Ile Arg Asn
            180                 185                 190

Ser Ser His Leu Pro Arg Asp Arg Leu Ala Glu Asp Phe Val Trp Ala
        195                 200                 205

Gln Trp Asp Leu Ser Glu Gln Arg Leu Tyr Tyr Ile Glu Leu Lys Glu
    210                 215                 220

Ser Arg Ser Ile Leu Lys Cys Ile Gln Phe Arg Ala Asp Glu Ser Phe
225                 230                 235                 240

Asn Leu Met Phe Glu Met Pro Leu Asp Ile Thr Leu Thr Gly Leu Arg
                245                 250                 255

Phe Lys Leu Val Asn Phe Gly Tyr Asp Tyr Arg Gln Asp Arg Glu Lys
            260                 265                 270

Leu Cys Asn Gln Pro Ser Leu Cys Ile Phe Thr Asn His Thr Gly Ser
        275                 280                 285

Leu Cys Met Cys Tyr Ser Pro Lys Ser Asp Ser Arg Glu Glu Ile Thr
    290                 295                 300

Tyr Ser Val Phe Tyr Leu His Lys Gly Tyr Arg Lys Ile Phe Thr Ala
305                 310                 315                 320

Ala Pro Gly Ser Ala Asp Ser Gln Val Thr Asn Gly Ala Asp Ser Gln
                325                 330                 335
```

```
Val Thr Asp Gly Ile Ala Phe Leu Asn Leu Gly Tyr Phe Val Ala Val
            340                 345                 350

Tyr Ser Pro Gly His Phe Leu His Leu Leu Asn Ile Gln His Pro Asp
        355                 360                 365

Leu Val Cys His Ser Leu Phe Leu Thr Gly Asn Asn Lys Ile Ala Ala
    370                 375                 380

Val Leu Pro Pro Ser Pro Leu Gln Ser Leu Pro Gly Ser Leu Val Leu
385                 390                 395                 400

Asp Cys Tyr Ser Gly Lys Val Tyr Arg Val Thr Leu Asp Gln Ser Tyr
                405                 410                 415

Leu Leu Arg Phe Leu Trp Asn Ala His Leu Asp Cys Glu Arg Met Ala
            420                 425                 430

Ala Leu His Cys Ile Leu Ser Cys Ser Gln Asp Pro Gly Phe Pro Glu
        435                 440                 445

Glu Gln Ile Ile Gln Trp Ile Ser Glu His Val Ser Ala Cys His Ser
    450                 455                 460

Phe Asp Leu Ile Gln Glu Phe Leu Ile Ala Ser Ser Tyr Trp Ser Val
465                 470                 475                 480

Tyr Ala Glu Leu Asp Asp Met Gly Met Leu Leu Gln Tyr Ser Ser Val
                485                 490                 495

Leu Thr Trp Asn Thr Glu Ile Pro Gly Ile Lys Phe Thr Thr Glu Glu
            500                 505                 510

Leu Pro Leu Pro Leu Met Lys Val Tyr Gly Leu Lys Gly Tyr Trp Ala
        515                 520                 525

Lys Leu Asn Ser Asn Leu Glu Tyr Ile Lys Tyr Thr Lys Pro His Leu
    530                 535                 540

His Tyr His Asn Ser Val Val Arg Arg Glu Trp His Asn Leu Ile Ser
545                 550                 555                 560

Glu Glu Arg Thr Gly Lys Arg Ser Thr Met Tyr Val Arg Asn Ile
                565                 570                 575

Leu Glu Asn Ala Met Lys Val Ile Ala Ser Met Glu Thr Arg Thr Leu
            580                 585                 590

Glu Pro Arg Leu Ile Pro Phe Leu Gln Glu Glu Asp Arg His Gln Arg
        595                 600                 605

Leu Leu Met Gly Leu Met Val Ser Glu Leu Arg Asp His Leu Leu Arg
    610                 615                 620

His Leu Gln Gly Val Glu Lys Lys Ile Glu Gln Met Val Leu Asp
625                 630                 635                 640

Tyr Ile Ser Lys Leu Leu Asp Leu Ile Trp Cys Leu Leu Glu Thr Ser
                645                 650                 655

Trp Arg Lys His Ser Met His Pro Leu Val Leu His Leu Asn Ser His
            660                 665                 670

Cys Ser Ala Ala Asp Phe Glu Val Phe His Leu Met Thr Arg Ile Leu
        675                 680                 685

Asp Ala Ala Ser Ser Leu Cys Leu Pro Leu Pro Gly Phe His Ser
    690                 695                 700

Leu His Thr Ile Leu Gly Val His Cys Leu Pro Leu Tyr Ser Leu Leu
705                 710                 715                 720

His Tyr Ile Asp Asn Gly Val Leu Leu Leu Thr Glu Thr Ala Val Thr
                725                 730                 735

Arg Leu Met Lys Asp Leu Asp Asn Ser Glu Lys Asn Glu Gln Leu Lys
            740                 745                 750

Phe Ser Ile Ile Val Arg Leu Pro Pro Leu Ile Gly Gln Lys Val Cys
```

```
            755                 760                 765
Arg Leu Trp Asp His Pro Met Ser Ser Asn Ile Ile Ser Arg Asn His
    770                 775                 780

Val Ala Arg Leu Leu Lys Asn Tyr Arg Lys Glu Pro Arg Asn Ser Met
785                 790                 795                 800

Ile Asp Lys Ser Ser Phe Pro Val Glu Phe Leu Pro Leu Asn Tyr Phe
                805                 810                 815

Ile Glu Ile Leu Met Gly Leu Glu Ser Ser Asn Gln Ala Leu Tyr Gly
                820                 825                 830

Phe Glu Gly His Asp Asn Val Asp Ala Glu Phe Val Glu Glu Ala Ala
            835                 840                 845

Leu Lys His Thr Thr Met Leu Leu Gly Leu
850                 855

<210> SEQ ID NO 5
<211> LENGTH: 846
<212> TYPE: PRT
<213> ORGANISM: Rattus norvegicus

<400> SEQUENCE: 5

Met Ala Leu Arg Leu Val Thr His Phe Asp Val Leu Ala Asp Val Leu
1               5                   10                  15

Pro Ser Leu Leu Val Gln Ala Ala Thr Ala Asp Glu Gly Asp Glu Gly
                20                  25                  30

Ala Glu Thr Thr Leu Gly Ser Leu Arg Val Leu Asn Ile Glu Arg Asn
            35                  40                  45

Gly Asp Ile Ile Tyr Thr Tyr Lys Asp Asn Lys Gly Asn Ala Val Phe
    50                  55                  60

Gly Ile Phe Asp Cys Gln Thr Arg Glu Asn Glu His Leu Tyr Thr Phe
65                  70                  75                  80

Glu Lys Asp Met Gln Ala Val Ser Cys Ser Val Asn Ser Glu Arg Thr
                85                  90                  95

Val Leu Ala Ala Ser Phe Ile Gln Tyr Thr Glu Gly Val Arg Ser Glu
            100                 105                 110

Leu Gln Pro Gly Ser Lys Cys Leu Thr Leu Leu Val Glu Ile His Pro
        115                 120                 125

Val Asn Asn Val Thr Val Leu Lys Ala Val Asp Ser Cys Val Trp Val
    130                 135                 140

Gln Phe Leu Tyr Pro Gln Ala Glu Ser His Leu Leu Ala Gln Asn His
145                 150                 155                 160

Leu Leu Leu Ile Ser Glu Glu Lys Tyr Ile Glu Arg Phe His Ile Gln
                165                 170                 175

Ile Thr Arg Glu Asp Gly Asn Arg Val Val Ile Arg Asn Ser Ser His
            180                 185                 190

Leu Pro Arg Glu Arg Ile Ala Glu Asp Phe Val Trp Ala Gln Trp Asp
        195                 200                 205

Val Ser Glu Gln Arg Ile His Tyr Ile Glu Leu Gln Glu Ser Arg Ser
    210                 215                 220

Ile Leu Lys Cys Val Gln Phe Trp Ala Asp Glu Ser Phe Thr Ile Met
225                 230                 235                 240

Phe Glu Met Pro Leu Asp Ile Ser Leu Ser Gly Leu Arg Phe Lys Leu
                245                 250                 255

Val Asn Phe Gly Tyr Asp Tyr Arg Gln Asp Gln Ala Lys Leu Cys His
            260                 265                 270
```

-continued

Gln Pro Ser Leu Cys Ile Phe Thr Asn His Thr Gly Ser Leu Cys Val
                275                 280                 285

Cys Tyr Ser Pro Lys Ser Asp Ser Trp Lys Glu Ile Thr Tyr Ser Val
    290                 295                 300

Phe Tyr Leu His Lys Gly Tyr Arg Lys Thr Phe Thr Val Ala Pro Gly
305                 310                 315                 320

Ser Thr Asp Ser Gln Val Ala Asn Gly Val Thr Phe Leu Asn Leu Gly
                325                 330                 335

Tyr Phe Val Ala Val Tyr Ser Pro Cys Arg Phe Leu His Leu Leu Asn
            340                 345                 350

Ile Arg His Pro Asp Leu Ile Cys His Ser Leu Phe Leu Thr Gly Asn
        355                 360                 365

Asn Lys Thr Ala Ala Val Leu Pro Pro Ser Pro Leu Gln Ser Leu Pro
    370                 375                 380

Gly Ser Leu Ile Leu Asp Cys Ser Ser Gly Lys Val Tyr Arg Ala Thr
385                 390                 395                 400

Leu Asp Gln Ser Tyr Leu Met Gly Phe Leu Trp Asn Ala Gln Leu Asp
                405                 410                 415

Cys Glu Lys Met Ala Ala Leu His Cys Ala Leu Ser Cys Asp Ser Asp
            420                 425                 430

Pro Gly Phe Pro Glu Gln Ile Val Gln Trp Val Ser Glu Arg Val Ser
        435                 440                 445

Ala Cys His Ser Phe Asp Leu Ile Gln Glu Phe Leu Ile Ala Ser Ser
    450                 455                 460

Tyr Trp Ser Val Tyr Pro Gly Leu Asp Asp Val Asp Leu Leu Leu Pro
465                 470                 475                 480

Tyr Ser Ser Val Leu Thr Trp Asp Thr Glu Ile Pro Gly Met Lys Leu
                485                 490                 495

Val Thr Glu Glu Leu Pro Leu Pro Leu Met Lys Val Tyr Ser Leu Lys
            500                 505                 510

Gly Tyr Trp Ala Lys Leu Asn Ser Asn Leu Glu Tyr Ile Lys Tyr Thr
        515                 520                 525

Lys Pro His Leu His Tyr His Asn Ser Val Val Arg Arg Glu Trp His
    530                 535                 540

Asn Leu Ile Ser Glu Glu Arg Thr Gly Lys Arg Arg Ser Thr Met Tyr
545                 550                 555                 560

Val Arg Asn Ile Leu Asp Asn Ala Val Lys Val Ile Ser Asn Met Glu
                565                 570                 575

Met Lys Thr Phe Glu Pro Arg Leu Ile Pro Leu Leu Gln Glu Glu Asp
            580                 585                 590

Arg His Gln Arg Leu Leu Met Gly Leu Met Val Ser Glu Leu Arg Asp
        595                 600                 605

His Leu Leu Arg His Leu Gln Gly Val Glu Lys Lys Ile Glu Gln
    610                 615                 620

Met Val Leu Asp Tyr Ile Ser Lys Leu Leu Asp Leu Val Trp Cys Leu
625                 630                 635                 640

Leu Glu Thr Ser Trp Arg Lys His Ser Val His Pro Trp Val Leu His
                645                 650                 655

Leu Asn Glu His Gly Ser Pro Ala Asp Phe Glu Val Phe His Leu Met
            660                 665                 670

Thr Arg Ile Leu Asp Ala Ala Ser Ser Leu Cys Phe Pro Leu Pro Pro
        675                 680                 685

Gly Phe His Ser Leu His Thr Ile Leu Gly Val His Cys Leu Pro Leu

```
                    690                 695                 700
Tyr Asn Leu Leu His Tyr Ile Asp Asn Gly Val Leu Leu Thr Glu
705                 710                 715                 720

Thr Val Val Thr Arg Leu Met Lys Asp Leu Asp Asn Ser Glu Lys Asn
                    725                 730                 735

Glu Lys Leu Lys Phe Ser Ile Ile Val Arg Leu Pro Pro Leu Ile Gly
                740                 745                 750

Gln Lys Val Cys Arg Leu Trp Asp His Pro Met Ser Ser Asn Ile Ile
            755                 760                 765

Ser Arg Asn His Val Ala Gln Leu Leu Lys Asn Tyr Lys Lys Glu Pro
        770                 775                 780

Gln Ser Ser Met Ile Asp Lys Ser Ser Phe Pro Val Glu Phe Leu Pro
785                 790                 795                 800

Leu Asn Tyr Phe Ile Glu Ile Leu Met His Leu Glu Ser Ser Asn Gln
                    805                 810                 815

Ala Leu His Gly Phe Glu Gly His Asp Asn Val Asp Ala Glu Phe Val
                820                 825                 830

Glu Glu Ala Ala Leu Lys His Thr Thr Ser Leu Leu Gly Leu
            835                 840                 845

<210> SEQ ID NO 6
<211> LENGTH: 857
<212> TYPE: PRT
<213> ORGANISM: Gallus gallus

<400> SEQUENCE: 6

Met Ala Val Ala Ala Pro Gln Gln Pro Ala Arg Cys Gly Gly Gln Arg
1               5                   10                  15

Pro Pro Glu Cys Gly Arg Val Gly Pro Arg Leu Arg Ala Leu Pro Ser
            20                  25                  30

Gly Gly Arg Arg Ser Gln Ala Gly Arg Glu Ser Pro Arg Ala Ala His
        35                  40                  45

Gly Ala Ala Ser Pro Leu Leu Pro Ser Gly Pro Gly Arg Leu Glu Ala
    50                  55                  60

Thr Gly Gly Arg Gly Asn Gly Gly Ala Ser Gly Arg Pro Gln Leu
65                  70                  75                  80

Arg Gly Leu Ser Pro Pro Ala Pro Leu Pro Cys Gly Gly Cys Ala Gly
                85                  90                  95

Pro Glu Leu Arg Gly Leu Thr Leu Ser Leu Cys Gly Gly Ser Ala Leu
            100                 105                 110

Asp Thr Ser Glu Lys Ser Ser Ala Leu Tyr Ile Val Asn Val Glu Arg
        115                 120                 125

Asn Gly Lys Ile Ile Tyr Thr Trp Lys Gly Asn Gln Arg Ser Thr His
    130                 135                 140

Ile Gly Leu Tyr Asp Leu Gln Thr Lys Glu Asn Glu His Leu Tyr Thr
145                 150                 155                 160

Phe Glu Lys Asp Leu Arg Ile Ile Ser Cys Ser Val Asn Ser Glu Arg
                165                 170                 175

Thr Leu Leu Ala Val Ser Phe Arg Gln Tyr Thr Glu Glu Arg Val
            180                 185                 190

Thr His Leu Leu Gln Ser Val Ser Lys Tyr Leu Ala Leu Leu Ile Glu
        195                 200                 205

Ile His Pro Ile Asn Asn Val Lys Val Leu Lys Ala Val Asp Ser Cys
    210                 215                 220
```

-continued

```
Val Arg Val Gln Phe Leu Tyr Pro Val Glu Asp Arg Asn Ser Ser Thr
225                 230                 235                 240

Glu Ser His Leu Leu Val Ser Glu Asp Lys Tyr Ile Glu Gln Phe
        245                 250                 255

Asp Ile His Val Ala Glu Glu His Arg Val Val Ile Gln Asn Ser
            260                 265                 270

Gly Gln Leu Pro Arg Ala Arg Val Ala Asp Leu Ile Trp Ala Gln
                275                 280                 285

Trp Asp Met Thr Glu Gln Arg Leu Phe Tyr Ile Val Pro Lys Glu Ser
290                 295                 300

Arg Ser Ile Leu Arg Cys Val Gln Phe Tyr Pro Asp Glu Asn Phe Asn
305                 310                 315                 320

Ser Thr Leu Glu Ser Gln Leu Asp Ile Ser Val Asn Asp Lys Arg Val
                325                 330                 335

Lys Leu Val Asn Phe Gly Tyr Asn Asp Cys Glu Asp Arg Asp Val Pro
                340                 345                 350

Pro Lys Ser Leu Asn Leu Gln Val Phe Thr Asn Lys Ala Gly Phe Ser
                355                 360                 365

Lys Thr Phe Thr Ala Ser Leu Glu Arg Pro Glu Thr Pro Gln Leu Lys
    370                 375                 380

Glu Val Ala Phe Leu Asn Leu Asp Tyr Tyr Val Ala Ala Tyr Leu Pro
385                 390                 395                 400

Gly Gln Phe Leu His Leu Leu Asn Ile Gln His Pro Asp Leu Leu Cys
                405                 410                 415

Tyr Ser Leu Phe Leu Thr Gly Glu Asp Ala Arg Ile Asp Met Leu Pro
                420                 425                 430

Asn Cys Ser Ile Gln Ser Pro Leu Val Ser Thr Val Leu Asp Cys Cys
            435                 440                 445

Ile Gly Arg Leu Tyr Ala Met Ser Ile Ser Asp Ser Ala Leu Leu Lys
        450                 455                 460

Tyr Leu Gln Asn Ser Lys Arg Asp Ser Glu Arg Leu Ala Ala Leu His
465                 470                 475                 480

Cys Ala Leu Leu Cys Val Arg Arg Thr Thr Asp Leu Glu Met Lys Ile
                485                 490                 495

Ile Trp Trp Ile Ser Glu Asn Leu Ser Thr Cys His Ser Phe Asp Pro
            500                 505                 510

Ile Gln Glu Phe Ile Ile Ala Ser Leu Tyr Cys Arg Met Cys Pro Glu
        515                 520                 525

Thr Asn Asn Leu Asp Lys Leu Leu Pro Tyr Thr Ser Leu Leu Asp Trp
530                 535                 540

Thr Gly Val Ile Pro Gly Val Ala Cys Ala Thr Asp Ile Ile Ser Leu
545                 550                 555                 560

Pro Val Leu Glu Met Gln Asn Ser Lys Gly Phe Trp Glu Lys Leu Asp
                565                 570                 575

Ser Asn Leu Glu Ser Val Lys Tyr Ala Glu Pro His Leu His Tyr His
            580                 585                 590

Asn Asn Val Leu Arg Arg Glu Trp Arg Asn Leu Ser Glu Glu Met Val
        595                 600                 605

Ala Gln Leu Lys Asp His Leu Met Arg His Leu Gln Tyr Val Gly Lys
    610                 615                 620

Lys Lys Ile Asp Gln Ile Val Leu Asp Tyr Val Ala Asn Leu Leu Asn
625                 630                 635                 640

Leu Val His Arg Ile Met Lys Glu Val Trp Lys Ile His Gln Leu His
```

```
                    645                 650                 655

Ser Cys Ile Phe Cys Phe Asp Glu Arg Gly Ser Glu Ala Glu Phe Arg
            660                 665                 670

Val Phe His Ile Met Ser Arg Ile Leu Glu Ala Ala Asn Gly Met Cys
            675                 680                 685

Met Pro Leu Pro Pro Gly Phe His Ser Leu His Leu Gly Leu Gly Val
        690                 695                 700

Arg Cys Leu Pro Leu His Thr Leu Leu His Tyr Ile Asp Asn Gly Val
705                 710                 715                 720

Leu His Leu Thr Glu Thr Cys Val Arg Lys Leu Leu Lys Asp Leu Asp
                725                 730                 735

Asp Asn Glu Lys Asn Glu Lys Leu Lys Phe Ser Ile Val Thr Arg Leu
            740                 745                 750

Pro Glu Val Thr Leu Asp Ala Leu Gly Leu Lys Ala Arg Gln Phe Trp
        755                 760                 765

Asp His Pro Val Asn Ala Asn Phe Arg Ala Arg Lys Tyr Val Lys Leu
            770                 775                 780

Leu Leu Glu Lys Leu Gly Asn Arg Gln Cys Ser Arg Pro Val Pro Glu
785                 790                 795                 800

Arg His Pro Val Cys Val Glu Phe Leu Pro Asn Tyr Leu Thr Asn
                805                 810                 815

Val Leu Ala Glu Ile Glu Ser Gln Gly Val His Leu Tyr Glu Lys Gln
            820                 825                 830

Asp His Ile Asn Val Arg Phe Val Glu Glu Ala Ala Leu Lys His Thr
            835                 840                 845

Met Met Leu Leu Gly Leu Arg Tyr Ser
        850                 855

<210> SEQ ID NO 7
<211> LENGTH: 13
<212> TYPE: PRT
<213> ORGANISM: Artificial Sequence
<220> FEATURE:
<223> OTHER INFORMATION: tryptic peptide

<400> SEQUENCE: 7

Leu Trp Asp His Pro Met Ser Ser Asn Ile Ile Ser Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: tryptic peptide

<400> SEQUENCE: 8

Asn His Val Thr Arg Leu Leu Gln Asn Tyr Lys Lys
1               5                   10
```